United States Patent
Tu et al.

(10) Patent No.: US 10,532,064 B2
(45) Date of Patent: Jan. 14, 2020

(54) BIOPHOSPHONATE COMPOUNDS AND GAMMA DELTA T CELL-MEDIATED THERAPY FOR TREATING EPSTEIN-BARR VIRUS-ASSOCIATED DISORDERS

(71) Applicant: The University of Hong Kong, Hong Kong (HK)

(72) Inventors: Wenwei Tu, Hong Kong (HK); Zheng Xiang, Hong Kong (HK); Yinping Liu, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 14/824,316

(22) Filed: Aug. 12, 2015

(65) Prior Publication Data

US 2016/0045521 A1 Feb. 18, 2016

Related U.S. Application Data

(60) Provisional application No. 62/036,487, filed on Aug. 12, 2014.

(51) Int. Cl.
*A61K 31/663* (2006.01)
*C12N 5/0783* (2010.01)

(52) U.S. Cl.
CPC .......... *A61K 31/663* (2013.01); *C12N 5/0636* (2013.01); *C12N 2501/999* (2013.01); *C12N 2531/00* (2013.01)

(58) Field of Classification Search
CPC ............ C12N 5/0636; C12N 2501/999; C12N 2531/00; A61K 31/666; A61K 31/00; A61K 31/663
See application file for complete search history.

(56) References Cited

U.S. PATENT DOCUMENTS

| | | | | |
|---|---|---|---|---|
| 6,696,427 B1 * | 2/2004 | Jomaa | .................... | A61K 31/663 514/75 |
| 2003/0171318 A1 * | 9/2003 | Morham | ............... | C07K 14/005 514/44 R |
| 2005/0196385 A1 * | 9/2005 | Romagne | .............. | C12N 5/0636 424/93.7 |
| 2013/0066051 A1 * | 3/2013 | Qiu | ....................... | C07K 14/245 530/387.3 |

FOREIGN PATENT DOCUMENTS

| WO | WO 2012054807 A2 * | 4/2012 | .............. | A61K 39/00 |
|---|---|---|---|---|
| WO | WO-2016005752 A1 * | 1/2016 | .............. | A61K 35/17 |

OTHER PUBLICATIONS

Kunzmann et. al., Blood, 2000, The American Society of Hematology, vol. 96(2), pp. 384-392.*
Landnneier et. al., Journal of Immunotherapy, 2009, Lippincott Williams and Wilkins, vol. 32, pp. 310-321 (Year: 2009).*
Baumforth et. al., Journal of Clinical Pathology: Molecular Pathology, 1999, British Medical Journals, vol. 52, pp. 307-322 (Year: 1999).*
Bonneville, et al., "Gammadelta T cell effector functions: a blend of innate programming and acquired plasticity", Nature Rev Immunol., 10:467-78 (2010).
Das, et al., "Vgamma2Vdelta2 T-cell receptor-mediated recognition of aminobisphosphonates", Blood, 98:1616-8 (2001).
Dharnidharka, et al., "New approaches to treating B-cell cancers induced by Epstein-Barr virus", NEJM, 372(6):569-71 (2015).
Funakoshi, et al., "Inhibition of human B-cell lymphoma growth by CD40 stimulation", Blood, 83:2787-94 (1994).
Kabelitz, et al., "Perspectives of gammadelta T cells in tumor immunology", Cancer Res., 67:5-8 (2007).
Kanakry and Ambinder, "EBV-related lymphomas: new approaches to treatment", Curr. Treat. Options Oncol., 14:224-36 (2013).
Khanna, et al., "Activation and adoptive transfer of Epstein-Barr virus-specific cytotoxic T cells in solid organ transplant patients with posttransplant lymphoproliferative disease", PNAS, 96:10391-6 (1999).
Kong, et al., "The NKG2D ligand ULBP4 binds to TCRgamma9/delta2 and induces cytotoxicity to tumor cells through both TCRgammadelta and NKG2D", Blood, 114:310-17 (2009).
Kotsiopriftis, et al., "Heat shock protein 90 expression in Epstein-Barr virus-infected B cells promotes gammadelta T-cell proliferation in vitro", J. Virol., 79:7255-61 (2005).
Kunzmann, et al., "Gamma/delta T-cell stimulation by pamidronate", N. Engl. J. Med., 340:737-8 (1999).
Lacerda, et al., "Human Epstein-Barr virus (EBV)-specific cytotoxic T lymphocytes home preferentially to and induce selective regressions of autologous EBV-induced B cell lymphoproliferations in xenografted C.B-17 scid/scid mice", J. Exp. Med., 183:1215-28 (1996).
Leen, et al., "Improving T cell therapy for cancer", Annu. Rev. Immunol., 25:243-65 (2007).
Li, et al., "Human $V^39V•2$-T cells efficiently kill influenza virus-infected lung alveolar epithelial cells", Cell Mol Immunol., 10(2):159-64 (2013).
Lim, et al., "Human plasmacytoid dendritic cells regulate immune responses to Epstein-Barr virus (EBV) infection and delay EBV-related mortality in humanized NOD-SCID mice", Blood, 109:1043-50 (2007).
Ma, et al., "A new model of Epstein-Barr virus infection reveals an important role for early lytic viral protein expression in the development of lymphomas", J. Virology, 85:165-77 (2011).
Qin, et al., "Phosphoantigen-expanded human gammadelta T cells display potent cytotoxicity against monocyte-derived macrophages infected with human and avian influenza viruses", J Infect Dis., 200(6):858-65 (2009).
Qin, et al., "Phenotypic and functional characterization of human $^3$T-cell subsets in response to Influenza A viruses", J Infect Dis., 205(11):1646-53 (2012).

(Continued)

*Primary Examiner* — Sarah Pihonak
(74) *Attorney, Agent, or Firm* — Pabst Patent Group LLP

(57) ABSTRACT

Aminobisphosphonate pamidronate (PAM) can control Epstein-Barr virus (EBV) associated disorders in humanized mice through a Vγ9Vδ2-T-cell dependent mechanism. This suggests a strong potential for a therapeutic approach using PAM to boost human Vγ9Vδ2-T-cell immunity against EBV associated disorders, such as the lymphoproliferative disease (LPD), posttransplant lymphoproliferative disorder (PLPD), Hodgkin's disease, Burkitt's lymphoma, and nasopharyngeal carcinoma (NPC).

21 Claims, 14 Drawing Sheets

(56) References Cited

OTHER PUBLICATIONS

Qin, et al., "Type 1 responses of human $V^3 9V'2$ T cells to influenza A viruses", J Virol., 85(19)10109-16 (2011).
Rooney, et al., "Use of gene-modified virus-specific T lymphocytes to control Epstein-Barr-virus-related lymphoproliferation", Lancet, 345:9-13 (1995).
Sicard, et al., "In vivo immunomanipulation of V gamma 9V delta 2 T cells with a synthetic phosphoantigen in a preclinical nonhuman primate model", J. immunology., 175:5471-80 (2005).
Speck and Longnecker, "Epstein-Barr virus (EBV) infection visualized by EGFP expression demonstrates dependence on known mediators of EBV entry", Arch Virol., 144:1123-37 (1999).
Strowig, et al., "Tonsilar NK cells restrict B cell transformation by the Epstein-Barr virus via IFN-gamma", PLoS Pathog., 4:e27 (2008).
Tu, et al., "The aminobisphosphonate pamidronate controls influenza pathogenesis by expanding a gammadelta T cell population in humanized mice", J Exp Med., 208(7):1511-22 (2011).
Tzartos, et al., "Association of innate immune activation with latent Epstein-Barr virus in active MS lesions", Neurology, 78:15-23 (2012).
Xiang, et al., "Targeted activation of human $V^3 9V'2$-T cells controls epstein-barr virus-induced B cell lymphoproliferative disease", Cancer Cell, 26(4):565-76 (2014).
Zheng, et al., "Human CD8+ regulatory T cells inhibit GVHD and preserve general immunity in humanized mice", Sci. Transl. Med., 5:168ra169 (2013).

* cited by examiner

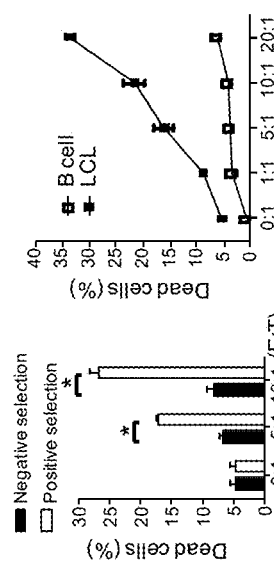
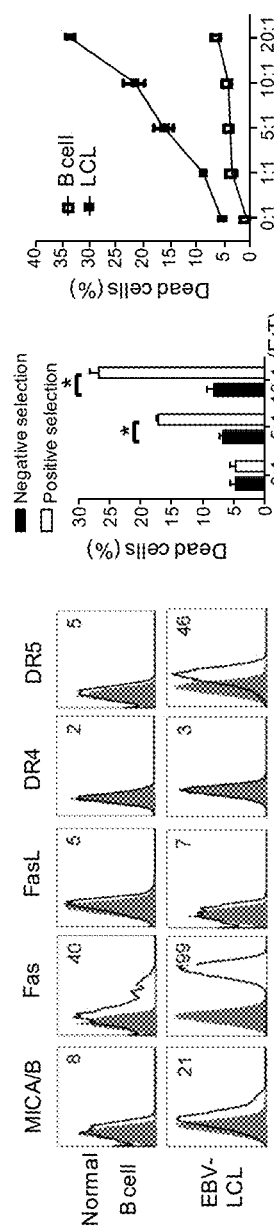
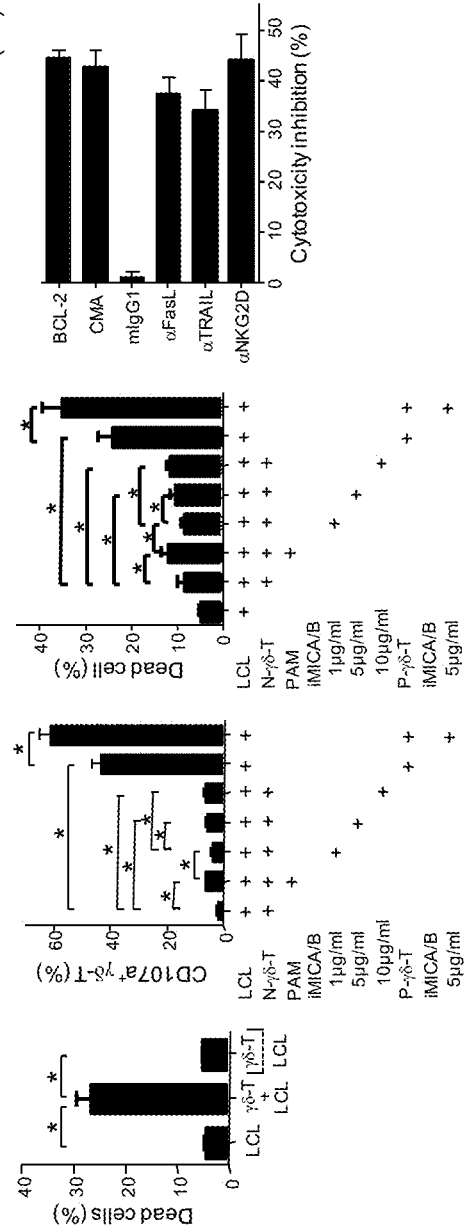

BIOPHOSPHONATE COMPOUNDS AND GAMMA DELTA T CELL-MEDIATED THERAPY FOR TREATING EPSTEIN-BARR VIRUS-ASSOCIATED DISORDERS

FIELD OF THE INVENTION

The invention is generally directed to treatment of Epstein-Barr virus (EBV)-associated disorders.

BACKGROUND OF THE INVENTION

Epstein-Barr virus (EBV) infects over 95% of the population worldwide, and is associated with several human malignancies, such as Hodgkin's disease, Burkitt's lymphoma, nasopharyngeal carcinoma (NPC), and EBV-positive diffuse large B-cell lymphoma. EBV is a herpesvirus that latently infects human B cells in most individuals by adulthood. Persistent EBV infection is generally subclinical in immunocompetent hosts (Cohen, N. Engl. J. Med. 343: 481-492 (2000)). However, immunocompromised patients are at high risk of developing EBV-induced B cell lymphoproliferative disorders (EBV-LPD) with significant morbidity and mortality (Shapiro et al., Blood 71:1234-1243 (1988)). Current treatment options for EBV-LPD include restoring the cellular immune responses to EBV and depleting the B cells with monoclonal antibodies or chemotherapy (Heslop et al., Blood 115:925-935 (2010); Khanna et al., Nat. Clin. Pract. Oncol. 2:138-149 (2005); Wagner-Johnston and Ambinder, Curr. Hematol. Malig. Rep. 2:249-254 (2007)). Restoration of cellular immune responses by adoptive transfer of ex vivo-generated EBV-specific cytotoxic T lymphocytes (CTL) has yielded promising results for treatment of EBV-LPD (Kanakry and Ambinder, Curr. Treat. Options Oncol. 14:224-236 (2013); Khanna et al., Proc. Natl. Acad. Sci. USA 96:10391-10396 (1999); Leen et al., Annu Rev. Immunol. 25:243-265; Long et al., Current opinion in immunology 23:258-264 (2011); Rooney et al., Lancet 345: 9-13 (1995)). However, its application for the treatment of EBV-LPD is limited by the difficulties in generating enough numbers of EBV-specific CTL in vitro and the lack of in vivo expansion of infused CTL in patients with bulky disease (Leen et al., 2007; Louis et al., Blood 113:2442-2450 (2009)). Antibody-mediated targeting of EBV-infected B cells has unwanted side-effects as anti-CD20 antibody also depletes normal B cells, causing prolonged hypogammaglobulinemia; and finally, chemotherapy leads to unwanted off-target toxicity and also causes general immunosuppression (Leen et al., 2007).

γδ-T cells are considered as innate-like T lymphocytes with NK cell characteristics (Born et al., Curr. Opin. Immunol. 18:31-38 (2006); Carding and Egan, Nat. Rev. Immunol. 2:336-345 (2002)). Various innate signals, either alone or in combination with ligand recognition via the TCR, induce γδ-T cells to display innate-like immune functions (Bonneville and Scotet, Curr. Opin. Immunol. 18:539-546 (2006); Born et al., 2006; Zheng et al., Cellular & molecular immunology 10:50-57 (2013a)). γδ-T cells make up 1-10% of T lymphocytes in the blood and peripheral organs in adult humans. Most γδ-T cells in the peripheral blood and lymphoid organs of healthy human adults are Vγ9Vδ2-T cells. Vγ9Vδ2-T cells can be specifically activated in an HLA-unrestricted manner by small non-peptidic phosphoantigens, which are metabolites of isoprenoid biosynthesis pathways (Beetz et al., Immunobiology 213:173-182 (2008)). Isopentenyl pyrophosphate (IPP), an intermediate produced through the mevalonate pathway, was found to selectively activate and expand human Vγ9Vδ2-T cells in vitro and in vivo (Alexander et al., Clin. Cancer Res. 14:4232-4240 (2008); Puan et al., Int. Immunol. 19:657-673 (2007)). Pharmacological compounds, such as the aminobisphosphonate pamidronate, commonly used for the treatment of osteoporosis, can induce intracellular accumulation of IPP, leading to activation and expansion of human Vγ9Vδ2-T cells (Bonneville and Scotet, 2006). Human Vγ9Vδ2-T cells can exert broad antiviral and antitumor activities in vitro and in humanized mice in vivo (Fournie et al., Cellular & molecular immunology 10:35-41 (2013); Qin et al., J. virology 85:10109-10116 (2011); Qin et al., J. Infect. Dis. 205:1646-1653 (2012); Tu et al., J. experimental medicine 208, 1511-1522 (2011)). However, whether these cells have similar effects on EBV and EBV-LPD remains unknown.

SUMMARY OF THE INVENTION

Aminobisphosphonate pamidronate (PAM) is commonly used for the treatment of osteoporosis. It is also used as a support medication to treat symptoms of cancer such as hypercalcemia (high blood calcium levels) or to decrease complications (such as fractures or pain) produced by bone metastasis.

As shown herein, PAM-expanded human Vγ9Vδ2-T cells efficiently kill Epstein-Barr virus-transformed autologous lymphoblastoid B cell lines (EBV-LCL) in vitro and in vivo. PAM can control EBV-associated disorders in humanized mice through a Vγ9Vδ2-T-cell dependent mechanism. This suggests a strong potential for a therapeutic approach using PAM to boost human Vγ9Vδ2-T-cell immunity against EBV-associated disorders, such as the lymphoproliferative disease (LPD), posttransplant lymphoproliferative disorder (PLPD), Hodgkin's disease, Burkitt's lymphoma, and nasopharyngeal carcinoma (NPC).

As such, the present invention discloses the use of PAM or PAM-expanded human Vγ9Vδ2-T cells to treat EBV associated disorders, and the therapeutic use of which to boost human Vγ9Vδ2-T-cell immunity against LPD, PLPD, Hodgkin's disease, Burkitt's lymphoma, and NPC.

In one aspect, the present invention provides methods of treating a subject having an EBV-associated disorder comprising administering to the subject an effective amount of PAM.

In another aspect, the present invention provides methods of treating a subject having an EBV-associated disorder comprising administering to the subject an effective amount of PAM-expanded Vγ9Vδ2-T cells.

In embodiments of the present invention, the EBV-associated disorder is selected from LPD, PLPD, Hodgkin's disease, Burkitt's lymphoma, and NPC. In some embodiments, the subject is a human. In some embodiments, PAM or PAM-expanded Vγ9Vδ2-T cells are administered with a pharmaceutically acceptable carrier.

In another aspect, the present invention provides pharmaceutical compositions comprising aminobisphosphonate pamidronate.

In yet another aspect, the present invention provides pharmaceutical compositions comprising aminobisphosphonate pamidronate-expanded Vγ9Vδ2-T cells.

The pharmaceutical compositions described herein may further comprise a pharmaceutically acceptable carrier and/or pharmaceutically acceptable excipients, additives, or adjuvants.

Kits are also provided in aspects of the present invention for use in activating and expanding a sub-population of immune cells. Such kits may comprise an expansion modulator, a solid support, and a selector.

In some embodiments, the sub-population of immune cells comprises Vγ9Vδ2-T cells. The expansion modulator may comprise a drug that has the ability to stimulate T cell expansion, such as aminobisphosphonate pamidronate. The solid support may comprise micro-beads. The selector may have an affinity to a particular population of immune cells and may comprise one or more antibody, one or more peptide, and/or one or more nucleic acid molecule. Further, the selector may be bound to a solid support. Additional embodiments of the kits provided herein may comprise at least one reagent and/or instructions for use thereof. The kits may additionally provide one or more reagents for use in flow cytometric analyses.

The methods, compositions and kits herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

BRIEF DESCRIPTION OF THE DRAWINGS

FIGS. 1A-1G show that Vγ9Vδ2-T cells kill EBV-LCL in vitro. FIG. 1A: Phenotypes of EBV-LCL and autologous normal human B cells. The white histograms represent MICA/B, Fas, FasL DR4 and DR5, and the gray histograms represent isotype controls. FIG. 1B, 1E, 1F: Pamidronate (PAM)-expanded Vγ9Vδ2 T cells were purified by positive selection (P-γδ-T) or negative selection (N-γδ-T) with anti-TCRγ/δ monoclonal antibody-conjugated micro-beads or TCRγ/δ+ T cell isolation kit, and then cultured with the autologous EBV-LCLs at different ratios for 4 hours. FIG. 1C, 1D, 1G: PAM-expanded Vγ9Vδ2 T cells purified by positive selection were co-cultured with autologous EBV-LCL or normal B cells at different E:T ratios (FIG. 1C) or an E:T ratio of 10:1 (FIGS. 1D and 1G) for 4-6 hours. FIG. 1D: The Vγ9Vδ2 T cells were directly co-cultured with or physically separated from autologous EBV-LCLs for 6 hours by using a transwell system. FIGS. 1E and 1F: P-γδT or N-γδ-T cells were pre-treated with or without immobilized MICA/B for 6 hours, and then co-cultured with autologous EBV-LCL at an E:T ratio of 10:1 for 4-6 hours. The percentages of dead cells among whole target cells (CD3⁻ population) identified as CD3⁻ PI⁺ (FIGS. 1B-1D, and 1F) and the surface expression of CD107a on Vγ9Vδ2 T cells (FIG. 1E) are shown. FIG. 1G: The perforin inhibitor CMA, granzyme B inactivator Bcl-2, anti-NKG2D (αNKG2D), anti-TRAIL (αTRAIL) and anti-FasL (αFasL) blocking antibodies, or their relevant isotype control (mouse IgG1, mIgG1) were used in co-culture of EBV-LCL and their autologous PAM-expanded Vγ9Vδ2 T cells. The cytotoxicity was shown as the percentage of inhibition relative to those without any treatment. All the data shown as mean±SEM are representative of four independent experiments. *p<0.05.

FIG. 2A-2C: Pamidronate (PAM)-expanded and activated Vγ9Vδ2-T cells in vitro. huPBMC were cultured in 10% FBS-RPMI1640 supplemented with 9 μg/mL of PAM; 500 IU/mL of rhIL-2 was added from day 3 post culture. The percentages and fold changes of Vγ9Vδ2-T cells in whole culture cells were examined by flow cytometry (FIG. 2A-2B). The data shown as mean±SEM are representative of 4 independent experiments. The phenotypes of freshly isolated Vγ9Vδ2-T cells and the cells expanded by PAM/IL2 or IL-2 alone after 20 days of culture are shown in FIG. 2C. The white histograms represent CD69, NKG2D, Fas, FasL, TRAIL, perforin and granzyme B, and the gray histograms represent their isotype controls. The data are representative of 4 independent experiments. FIG. 2D: EBV-LCL alone could not efficiently expand Vγ9Vδ2-T cells. The CFSE labeled-PBMCs were co-cultured with or without the autologous EBV-LCL at a ratio of 10:1 for 3 days. The absolute number of Vγ9Vδ2-T cells after 3 days of co-culture is shown (FIG. 2D). The data shown as mean±SEM are representative of 3 independent experiments. ns, no significant difference. FIG. 2E: Immobilized MICA/B enhanced the expression of EBV-LCL recognition receptors and cytotoxic molecules in Vγ9Vδ2-T cells, especially for the cells sorted through positive selection. PAM-expanded Vγ9Vδ2-T cells were purified by positive selection (P-γδ-T) or negative selection (N-γδ-T) with an anti-TCRγ/δ Micro-Bead or TCRγ/δ+ T cell isolation kit, and then pre-treated with or without immobilized MICA/B for 6 hours. The phenotypes of Vγ9Vδ2-T cells were determined by flow cytometry (FIG. 2E). Graphs, from top to bottom, for each marker are N-γδ-T, N-γδ-T+PAM (5 μg/ml), N-γδ-T+rMICA/B (1 μg/ml), N-γδ-T+rMICA/B (5 μg/ml), N-γδ-T+rMICA/B (10 μg/ml), P-γδ-T, P-γδ-T+rMICA/B (5 μg/ml). Data are representative of 4 independent experiments. FIG. 2F: PAM did not show any cytotoxic activities against EBV-LCL. The EBV-LCL were cultured in the medium with or without PAM (9 μg/mL) for 24, 48, and 72 hours. The percentage of dead cells among whole cells was identified as PI⁺ cells. The data shown as mean±SEM are representative of 4 independent experiments (FIG. 2F). FIG. 2G: PAM enhanced the expression of EBV-LCL recognition receptors and cytotoxic molecules in Vγ9Vδ2-T cells. The PBMCs were co-cultured with the autologous EBV-LCL at a ratio of 10:1 in the presence or absence of PAM (9 μg/mL) for 5 days. The phenotypes of Vγ9Vδ2-T cells were determined by flow cytometry. The white histograms represent CD69, NKG2D, Fas, FasL, TRAIL, CD107a, perforin and granzyme B, and the gray histograms represent their isotype controls. Data are representative of 4 independent experiments.

FIG. 3A: Protocol of establishment of EBV-LPD mouse model and evaluation of the antitumor activity of Vγ9Vδ2-T cells in vivo. Rag2⁻/⁻γc⁻/⁻ mice were inoculated s.c. with EGFP-expressing EBV-LCL. The PAM-expanded autologous Vγ9Vδ2-T cells were adoptively transferred i.v. into Rag2⁻/⁻γc⁻/⁻ mice post inoculation with EBV-LCLs at day 0, 7, 14 and 21. The mice treated with an equivalent volume of PBS were used as the control group. The subcutaneous tumors were monitored by in vivo imagine system at the indicated time. Whole body fluorescence images in mice treated with PAM-expanded Vγ9Vδ2-T cells or PBS (n=5 per group) were prepared. FIG. 3B-3D: After treatment with PAM-expanded Vγ9Vδ2-T cells (n=10) or PBS (n=11), the survival (FIG. 3B), tumor incidence (FIG. 3C) and tumor volume (mean±SEM) at autopsy (FIG. 3D) were measured. *p<0.05.

FIG. 5A: Protocol for evaluation of the therapeutic effect of Vγ9Vδ2-T cells EBV-LPD in tumor-bearing Rag2$^{-/-}$γc$^{-/-}$ mice. EGFP$^+$ EBV-LCL were inoculated into Rag2$^{-/-}$γc$^{-/-}$ mice s.c. Twenty one days later, half of these tumor-bearing mice were adoptively transferred with the PAM-expanded autologous Vγ9Vδ2-T cells i.v. at the indicated time and another half of these mice were treated with PBS as the control. Whole body fluorescence images in mice before treatment with Vγ9Vδ2-T cells or PBS were prepared. FIGS. 5B and 5C: After treatment with Vγ9Vδ2-T cells (n=6) or PBS (n=6), the tumor volume (FIG. 5B) and survival (FIG. 5C) in tumor-bearing Rag2$^{-/-}$γc$^{-/-}$ mice were measured at indicated time. Data are mean±SEM. ns, no significant difference; *p<0.05.

FIG. 7A: DiR-labeled PAM-expanded Vγ9Vδ2-T cells were adoptively transferred into Rag2$^{-/-}$γc$^{-/-}$ mice with subcutaneous tumors after EGFP$^+$ EBV-LCL inoculation. The migration and accumulation of Vγ9Vδ2-T cells (DiR-labeled) in the tumor sites (EGFP$^+$) were monitored at indicated times after injection. The fluorescence intensity of DiR signal was measured in selected areas. Data are means±SEM. Infiltrated Vγ9Vδ2-T cells within tumor tissues at 12 hours after adoptive transfer of Vγ9Vδ2-T cells was analyzed by confocal fluorescence microscope. FIG. 7B: Vγ9Vδ2-T cells were pre-incubated with αCCR5, or mIgG2a for 30 minutes and placed in the upper well. The supernatants from EBV-LCL were added into the lower well. The percentages of cells (means±SEM) that have migrated from the upper well after 4 hours are shown (n=4). FIG. 7C: The concentrations of chemokines (means±SEM) in the supernatants from EBV-LCL were measured (n=4). FIG. 7D: The surface expression of CCR5 on Vγ9Vδ2-T cells after treatment with anti-CCR5 blocking antibody (αCCR5) or its isotype control (mouse IgG2a, mIgG2a) for 2 hours is shown. FIG. 7E: DiR-labeled PAM-expanded Vγ9Vδ2-T cells were pre-treated with αCCR5 or mIgG2a for 2 hours, and then adoptively transferred into EGFP$^+$ EBV-LCL subcutaneous tumor-bearing mice. The migration and accumulation of Vγ9Vδ2-T cells (DiR-labeled) in the tumor sites (EGFP$^+$) were detected at 24 hours after injection. The fluorescence intensity of DiR signal was measured in the indicated area with dashed lines (FIG. 7E). Data are means±SEM. Data represent 3-4 independent experiments. ns, no significant difference. ND, undetectable; *p<0.05; **p<0.01.

FIG. 8A: Protocol for the control of EBV-LPD by pamidronate (PAM) in humanized mice. Humanized mice were treated with PAM or PBS at day 0, 7, 14, 21, 28 after inoculation of EBV-LCL. FIG. 8B-8D: After treatment with PAM (n=8) or PBS (n=7), the survival (FIG. 8B), tumor incidence (FIG. 8C) and tumor volume (FIG. 8D) were measured at the indicated time. Data are means±SEM. *p<0.05.

FIG. 10A shows that post 20 days of in vitro culture in the presence of PAM and IL-2, the percentage of Vγ9Vδ2-T cells within the PBMCs increased to 67-95% (mean, 82%) and FIG. 10B shows the Vγ9Vδ2-T cells were expanded by 156-309-fold (mean, 198-fold). Data are representative for 4 independent experiments (FIGS. 10A and 10B). By contrast, the IL-2 could not induce the expansion of Vγ9Vδ2-T cells in the absence of PAM (FIGS. 10A and 10B).

FIG. 11A shows expansion kit-expanded Vγ9Vδ2-T cells cultured with the autologous EBV-LCLs at different ratios for 4 hours before and after purification by selection reagent A and B. FIG. 11B shows the percentages of dead LCLs among the target cells (CD3$^-$ population) identified as CD3$^-$ and PI$^+$ for 4 independent experiments.

DETAILED DESCRIPTION OF THE INVENTION

Figure 2A:
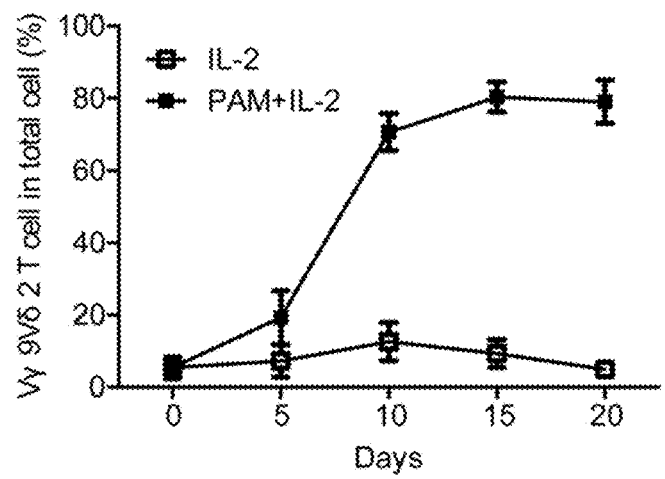
FIGS. 2A-2G show the effects of pamidronate on the activation, expansion and cytotoxic activity of Vγ9Vδ2-T cells.

The present invention provides compositions, methods, and kits for treating EBV-associated disorders.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Prior to setting forth the invention in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

I. Definitions

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to an animal. Typically, the terms "subject" and "patient" may be used interchangeably herein in reference to a subject. As such, a "subject" includes an animal that is being treated for a disorder/disease or the recipient of a mixture of components as described herein. The term "animal," includes, but is not limited to, mouse, rat, dog, guinea pig, cow, horse, chicken, cat, rabbit, pig, monkey, chimpanzee, and human.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a human.

The term "effective amount" of a composition refers to a nontoxic but sufficient amount of the composition to provide the desired result. The exact amount required will vary from subject to subject, depending on the species, age, and general condition of the subject, the mode of administration, and the like. Thus, it is not possible to specify an exact "effective amount." However, an appropriate effective amount can be determined by one of ordinary skill in the art using only routine experimentation.

The dosages or amounts of the disclosed compositions are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

II. Methods

Current treatment strategies for EBV-LPD include restoring EBV-specific cytotoxic T lymphocytes (CTL) and depleting the B cells with monoclonal antibodies or chemotherapy. However, restoration of EBV-specific CTL is limited by the difficulties in generating enough numbers of EBV-specific CTL in vitro and the lack of in vivo expansion of infused CTL. Antibody-mediated targeting EBV-infected B cells and chemotherapy have unwanted side-effects and lead to general immunosuppression. The present invention shows that aminobisphosphonate pamidronate (PAM) (also referred to herein as "pamidronate") can control EBV-LPD by enhancing human Vγ9Vδ2-T-cell immunity. As PAM has been already used for decades in osteoporosis treatment, this new application of PAM potentially offers a safe and readily available option for the treatment of EBV-LPD.

Recently, humanized mice with human peripheral blood mononuclear cells (huPBMC) were established. These mice contain functional human T and B cells, including a similar percentage of Vγ9Vδ2-T cells in peripheral blood as seen in humans (Tu et al., 2011; Zheng et al., Sci. Transl. Med. 5:168ra169 (2013b)). The effect of PAM-expanded human Vγ9Vδ2-T cells on the growth of EBV-transformed autologous lymphoblastoid B cell lines (EBV-LCL) in vitro and in immunodeficient Rag2$^{-/-}$γc$^{-/-}$ mice was investigated, and the role of PAM in the control of EBV-LPD in humanized mice was determined.

In one aspect, the present invention provides methods of treating a subject having an EBV-associated disorder comprising administering to the subject an effective amount of PAM.

In another aspect, the present invention provides methods of treating a subject having an EBV-associated disorder comprising administering to the subject an effective amount of PAM-expanded Vγ9Vδ2-T cells.

In embodiments of the present invention, the EBV-associated disorder is selected from lymphoproliferative disease (LPD), posttransplant lymphoproliferative disorder (PLPD), Hodgkin's disease, Burkitt's lymphoma, and NPC. In some embodiments, the subject is human. In some embodiments, PAM or PAM-expanded Vγ9Vδ2-T cells are administered with a pharmaceutically acceptable carrier. Furthermore, it would be understood by those skilled in the art that the therapeutic methods described would not only apply to treatment in a subject, but could be applied to cell cultures, organs, tissues, or individual cells in vivo, ex vivo or in vitro.

III. Compositions

In another aspect, the present invention provides pharmaceutical compositions comprising PAM.

In yet another aspect, the present invention provides pharmaceutical compositions comprising PAM-expanded Vγ9Vδ2-T cells.

The pharmaceutical compositions described herein may further comprise a pharmaceutically acceptable carrier and/or pharmaceutically acceptable excipients, additives, or adjuvants for administration to a subject for treatment or prevention.

The carrier, adjuvant, and additives with which the compositions described herein are administered and/or packaged can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition may also contain wetting or emulsifying agents or suspending/diluting agents, or pH buffering agents, or agents for modifying or maintaining the rate of release of the compositions described herein. These compositions can take the form of solutions, suspensions, emulsions, tablets, pills, capsules, powders, sustained-release formulations and the like. Formulations can include standard carriers such as pharmaceutical grades of mannitol, lactose, sodium saccharine, starch, magnesium stearate, cellulose, magnesium carbonate, etc. Such compositions will contain an effective amount of the compound(s) or cells together with a suitable amount of carrier so as to provide the proper form to the patient based on the mode of administration to be used.

If for intravenous administration, the compositions/cells are packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachette indicating the amount of active agent. If the composition/cells are to be administered by infusion, they can be dispensed with an infusion bottle containing sterile pharmaceutical grade water or saline. Where the composition or cells is/are administered by injection, an ampoule of sterile water or saline can be provided so that the ingredients may be mixed prior to injection.

IV. Kits

The compositions described above, as well as other materials, can be packaged together in any suitable combination as a kit useful for performing, or aiding in the performance of, the disclosed methods. It is useful if the components in a given kit are designed and adapted for use together in the disclosed methods. For example, kits of the present invention are for activating and expanding a sub-population of immune cells. The kits may comprise an expansion modulator, a solid support, and a selector.

In some embodiments, the sub-population of immune cells comprises Vγ9Vδ2-T cells. The expansion modulator may comprise a drug that has the ability to stimulate T cell expansion, such as aminobisphosphonate pamidronate. The solid support may comprise micro-beads. The selector may have an affinity to a particular population of immune cells and may comprise one or more antibody, one or more peptide, and/or one or more nucleic acid molecule. Further, the selector may be bound to a solid support. Also, the kits may include one or more containers filled with reagent(s) and/or one or more components of the invention. One or more container of the kits provided may also comprise an antibody, peptide, or nucleic acid molecule, preferably in a purified form. In some embodiments, the components may be provided in separate containers for mixing prior to use. The kits may also comprise a control composition for use as a control reagent in experimentation. As it would be understood by those skilled in the art, detection or labeling methodologies may be used in the kits provided when utilized in an experimental or laboratory setting. To that end, the kits may additionally provide one or more reagents for use in flow cytometric analyses.

The following is an example of instructions that can be included in a kit and also provides a description of examples of the disclosed materials, reagents, and methods.

1.1 Background

γδ-T cells make up 1-10% of T lymphocytes in the blood and peripheral organs in adult humans. Most γδ-T cells in the peripheral blood and lymphoid organs of healthy human adults are Vγ9Vδ2-T cells (Chien et al., *Ann Rev Immunol* 32:121-155 (2014)). Pharmacological compounds, such as the aminobisphosphonate pamidronate commonly used for the treatment of osteoporosis, can induce intracellular accumulation of IPP, leading to activation and expansion of human Vγ9Vδ2-T cells. Human Vγ9Vδ2-T cells can exert broad antiviral and antitumor activities in vitro and in humanized mice in vivo (Xiang et al., *Cancer Cell* 26(4): 565-576 (2014); Li et al., *Cell Mol Immunol* 10(2):159-164 (2013); Qin et al., *J Infect Dis* 205(11):1646-1653 (2012); Tu et al., *J Exp Med* 208(7):1511-1522 (2011); Qin et al., *J Virol* 85(19)10109-10116 (2011); Qin et al., *J Infect Dis* 200(6):858-865 (2009)). Aminobisphosphonate pamidronate can control EBV-LPD by enhancing human Vγ9Vδ2-T-cell immunity. Pamidronate offers a safe and readily available option for the treatment of EBV-LPD (Dharnidharka et al., *NEJM* 372(6):569-571 (2015); Xiang et al., *Cancer Cell* 26(4):565-576 (2014)).

This kit is particular in expanding and selecting human Vγ9Vδ2-T cells with high purity and significant activation level for clinical application in treating EBV-associated disorders, such as the EBV-caused B cell lymphoproliferative disease (EBV-LPD). First, the Vγ9Vδ2-T cells in human peripheral blood mononuclear cells (hPBMCs) are specially expanded by using expansion reagent A (Pamidronate) and then proliferation of Vγ9Vδ2-T cells is supported by expansion reagent B (human recombinant Interleukin-2). Second, the expanded-human Vγ9Vδ2-T cells are selected and purified by using selection reagent A (anti-TCR γ/δ hapten antibody) and B (anti-hapten microbeads). Finally, the purity or percentage of Vγ9Vδ2-T cells is detected by detection reagent (A with B or A with C). In a preferred embodiment, detection reagent A consists of PE anti-human CD3 antibody, detection reagent B consists of APC anti-human TCR Vγ9 antibody, and detection reagent C consists of FITC anti-human TCR Vδ2 antibody.

1.2 Example Applications

Expansion, purification and activation of human Vγ9Vδ2-T-cells from in vitro-expanded cell culture using Pamidronate. Large quantity of highly purified-human Vγ9Vδ2-T-cells is collected for clinical usage in treating EBV-associated diseases, especially the EBV-LPD.

Functional analysis of human Vγ9Vδ2-T-cells with high activation and cytotoxic activity, e.g. studies on cytokine secretion, antigen recognition and cell signaling.

1.3 Essential Reagents and Instruments

Cell culture medium: Roswell Park Memorial Institute (RPMI)-1640 (Invitrogen) containing 10% heat-inactivated fetal bovine serum (FBS; Invitrogen).

Buffer: Phosphate buffered saline (PBS) pH 7.2. In the selection step, the PBS is supplemented with 0.5% FBS and keep cold during performing experiment.

Selection columns and separator: Purification of Vγ9Vδ2-T-cells by using LS columns (MACS), and Vγ9Vδ2-T-cells can be enriched through magnetic separator (MACS).

2. Protocol 2.1 Human Peripheral Blood Mononuclear Cell Preparation

The hPBMCs are isolated from buffy coat preparation or anticoagulated peripheral blood by Ficoll-paque (GE Health life Science) gradient centrifugation.

2.2 Expansion of Human Vl/91782-T Cells
 1. Wash the isolated PBMCs with pre-warmed PBS, re-suspend the cells pellet with 50 ml of pre-warmed PBS.
 2. Determine the cell number.
 3. Aliquot 10~20×$10^6$ cells for each well (6-well plate) and re-suspend in 5 ml of cell culture medium supplemented with 15 μl of expansion reagent A.
 4. Incubate the cells at 37° C., 5% $CO_2$ for 2 days.
 5. On day 3, collect the cells and centrifuge at 1200 rpm for 10 min. Then cells are re-suspended in the fresh cell culture medium contained with 15 ul of expansion reagent A and 25 μl of expansion reagent B.
 6. 25 μl of expansion reagent B are added every third day from day 3. After 15~20 days of culture, the expanded-Vγ9Vδ2-T-cells can be collected for the future use.

2.3 Selection of Human Vγ9V82-T Cells
 1. Wash the expanded-Vγ9Vδ2-T-cells with warm PBS, and then re-suspend in the PBS supplemented with 0.5% FBS.
 2. Determine the cell number.
 3. Collect the cells by centrifugation at 1200 rpm for 10 min. Discard the supernatant completely.
 4. The cells are re-suspended in 40 μl of PBS per $10^7$ total cells.
 5. 10 μl of selection reagent A is needed for $10^7$ cells.
 6. Mix well and incubate for 10 min at 4° C.
 7. Add 30 μl of PBS and 20 μl of selection reagent B per $10^7$ cells.
 8. Mix well and incubate for 15 min at 4° C.
 9. Wash cells by adding 1-2 ml of PBS per $10^7$ cells and centrifuge at 1200 rpm for 10 min. Pipette off supernatant completely.
 10. Re-suspend up to $10^7$ cells in 500 μl of PBS.
 11. Place the selection column in the magnetic field of a selection separator.
 12. Prepare the column by rinsing with 3 ml of PBS.
 13. Wash the column three times by PBS.
 14. Remove column from the separator and place it on a suitable collection tube.
 15. Pipette 5 ml of PBS onto the column. Immediately flush out of fraction with Vγ9Vδ2-T-cells by firmly applying the plunger supplied with column.
 16. Determine the cell number.

2.4 Detection of Human Vγ9Vδ2-T Cells
 1. Collection of 1.0×$10^6$ cells from the cell culture or purified-Vγ9Vδ2-T-cells for detecting the percentage or purity of Vγ9Vδ2-T-cells.
 2. Wash the cells by 1 ml of PBS and centrifuge at 1200 rpm for 10 min.
 3. Discard the supernatant and re-suspend the cells in 100 μl of PBS.
 4. 5 μl of detection reagent A and B (A and C OR B and C) are added in the solution. Then incubate at room temperature in dark for 15 min.
 5. Wash the cells by 1 ml of PBS and centrifuge at 1200 rpm for 10 min.
 6. Re-suspend the cells in 200 μl of PBS, and then data collected by flow cytometry (BD LSRII).
 7. The data analyzed by using Flowjo software (Tree Star).

EXAMPLES

Materials and Methods

Establishment of ERV-LCL In Vitro.

huPBMC were isolated from buffy coats of EBV-seropositive health donors after informed consents were obtained. The research protocol was approved by the Institutional Review Board of the University of Hong Kong/Hospital Authority Hong Kong West Cluster. EBV-LCL were established as described before (Lacerda et al., J. Exp. Med. 183:1215-1228 (1996)). Briefly, huPBMC were infected with supernatants from the EBV-secreting cell line B95-8 or B95.8EBfaV-GFP, carrying an enhanced green fluorescent protein (EGFP, kindly provided by Diane Hayward, Johns Hopkins University, Baltimore) (Speck and Longnecker, Arch Virol 144:1123-1137 (1999)), and then cultured in the RPMI 1640 supplemented with 15% heat-inactivated FBS.

Expansion and Purification of Vγ9Vδ2-T Cells In Vitro.

Pamidronate-expanded Vγ9Vδ2-T cells were generated as described before (Tu et al., 2011). Briefly, huPBMC were cultured in RPMI 1640 medium supplemented with 10% FBS. Pamidronate was added at day 0 and day 3 to a final concentration 9 μg/ml. Recombinant human IL-2 (Invitrogen) was added to a final concentration of 500 UI/ml every 3 days from day 3. After 14 days of culture, the Vγ9Vδ2-T cells were purified by positive selection or negative selection with anti-TCRγ/δ MicroBead or TCRγ/δ$^+$ T cell isolation kit (Miltenyi Biotec). The purity of Vγ9Vδ2-T cells as determined by flow cytometry using anti-CD3 and anti-Vδ2 mAbs, was consistently >97%.

Establishment of EBV-LPD Model and Treatment of EBV-LPD in Humanized and Rag2$^{-/-}$γc$^{-/-}$ Mice.

All animal studies were approved and performed in compliance with the guidelines for the use of experimental animals by the Committee on the Use of Live Animals in the Teaching and Research, the University of Hong Kong. Humanized mice were generated in 4-5 weeks old male or female Rag2$^{-/-}$γc$^{-/-}$ mice by reconstitution of EBV seropositive whole huPBMC or Vγ9Vδ2-T-cell-depleted huPBMC as we described before (Tu et al., 2011). After 4 weeks of huPBMC transplantation, mice were successfully accepted engraft and became stable with functional human immune system (Tu et al., 2011), and then used for establishment of EBV-LPD. Humanized mice or 6-8 week old Rag2$^{-/-}$γc$^{-/-}$ mice were inoculated s.c. with EBV-LCL or EGFP-expressing EBV-LCL (0.1×10$^6$/mouse). For Rag2$^{-/-}$γc$^{-/-}$ mice, pamidronate-expanded autologous Vγ9Vδ2-T cells (10×10$^6$/mouse) in 200 μl of PBS were adoptively transferred i.v. into mice post inoculation with EBV-LCLs at indicated time. For humanized mice, a human equivalent dose of PAM (10 mg/kg body weight; Pamisol; Hospira Austrilia Pty Led) was injected i.p. at indicated time. The mice treated with an equivalent volume of PBS were used as controls. The signs of disease (loss of activity, weight loss, ruffled hair, palpable tumors, and ascites) and survival of mice were monitored. Mice with more than 17 mm of diameter subcutaneous tumor were sacrificed and counted as dying. Otherwise, mice were followed for 100 or 170 days and then killed. All mice were examined for postmortem evidence of tumor. The tumors and organs were collected for histology and immunohistochemistry assays.

In Vivo Tracking with DiR-Labeled Vγ9Vδ2-T Cells.

Vγ9Vδ2-T cells were stained with DiR (Invitrogen), and then these DiR-labeled cells were adoptively transferred intravenously into subcutaneous EGFP-EBV tumor bearing mice. The migration and accumulation of Vγ9Vδ2-T cells were visualized and analyzed with a TM 2 in vivo imaging system (CRI Maestro) at indicated time. After 12 hr, some mice were killed, and tumor sections were snapped frozen and stained with anti-human TCR γ/δ mAb (5 μg/ml; B-1, Biolegend). These cryostat sections were analyzed by Confocal Laser Scanning Microscope (LSM 700, Carl Zeiss).

Chemotaxis Assay.

The in vitro migration of purified Vγ9Vδ2-T cells was assessed in a transwell system (24-well; pore size, 5.0 μm; polycarbonate membranes; Corning-Costar) as we described before (Qin et al., 2011). Briefly, supernatants from EBV-LCL after 24 hr of culture in RPMI 1640 medium were collected, and loaded in the lower compartment. A total of 100 μl of autologous Vγ9Vδ2-T cells (4×10$^5$) in serum-free RPMI 1640 medium was added to the upper compartment of the chamber. After 4 hr, the cells that had migrated through the membrane to the lower compartment were collected and counted by flow cytometry with counting beads. The migration of Vγ9Vδ2-T cells in control group (γδ-T cells alone) was set to 100% and the results obtained from other treatment group or isotype control group were expressed as a percentage of the control. In blocking experiments, Vγ9Vδ2-T cells were pre-incubated for 30 min with either anti-CCR5 mAb (2 μg/ml; clone 2D7, BD) or isotype control mouse IgG2a (2 μg/ml) mAb.

Cytotoxic Assay.

The death of EBV-LCL (target) was analyzed by flow cytometry after 4-6 hr of co-culture with autologous Vγ9Vδ2-T cells (effector) at different E:T ratios. In some experiments, a transwell system (24 wells; pore size, 0.4 mm; Corning-Costar) were used to separate Vγ9Vδ2-T cells from EBV-LCL as we did before (Qin et al., 2009). In some experiments, neutralization antibodies anti-NKG2D (10 μg/ml; 149810, R&D system), anti-Fas-L (10 μg/ml; NOK-1, Biolegend), anti-TRAIL (10 μg/ml; RIK-2, Biolegend) and isotype control mouse IgG1 (10 μg/ml) were used for blocking NKG2D-, FasL- and TRAIL-mediated pathways (Qin et al., 2009). For MICA/B immobilization, 24-well plated were coated with recombinant MICA/B proteins (Sino Biological Inc.) overnight. The plates were carefully washed to remove the unbound protein and then incubated with Vγ9Vδ2-T cells for 6 hr. For blocking perforin and granzyme B, the perforin inhibitor concanamycin A (CMA) (1 μg/ml; Sigma) and the granzyme B inactivator Bcl-2 (1 μg/ml; R&D Systems) were used as we did before (Qin et al., 2009). Cytotoxicity was analyzed by flow cytometry and calculated as the percentage of inhibition relative to that in controls Cells were stained with anti-CD3 to identify Vγ9Vδ2-T cells and PI was used to identify dead cells. The death of EBV-LCL was shown as the percentage of PI$^+$ cells in the CD3$^-$ population (Qin et al., 2009).

Histopathology and Immunohistochemistry.

Samples of tumors and organs to be analyzed were fixed in 10% formalin, embedded in paraffin, sectioned and stained with hematoxylin and eosin. To investigate the presence of EBV, tissues were stained with mouse anti EBV LMP1 (ab58938, Abcam) and the presence of human B cells in tissues was assessed using rabbit anti human CD20 (EP459Y, Abcam) by immunoperoxidase techniques. The proliferative rate of cells and the aggressive nature of lymphomas were indicated by histological staining of Ki67 (ab136912, Abcam). Visualization of immunostaining was used by a diaminobenzidine detection kit (DAB-0031, Maixin) and then the sections were counterstained with hematoxylin.

In Situ Hybridization.

In situ hybridization of paraffin sections from tumors and mouse organs to detect Epstein-Barr encoded small RNAs type 1 and 2 (EBER-1/2) was performed using DIG-HRP REMBRANDT® EBER ISH kit (Tzartos et al., Neurology 78:15-23 (2012)) (A500K.9901, Panpath) according to the manufacture's protocol.

Flow Cytometric Analysis.

Cells were stained for surface markers with the following antibodies: anti-CD3 (HIT3a), anti-TCR V62 (B6), anti-CD69 (FN50), anti-NKG2D (1D11), anti-Fas (DX2), anti-CD107a (H4A3), anti-FasL (NOK-1), anti-TRAIL (RIK-2), anti-MICA/B (6D4), anti-DR4 (DJR1), anti-DR5 (DJR2-4), anti-CCR5 (2D7). For the intracellular staining, cells were fixed, permeabilized, and then stained with anti-perforin (δG9) and anti-granzyme B (GB11) antibodies (BD) or their relevant isotype controls as described previously (Qin et al., 2009; Tu et al., 2011). All samples were acquired on a FACSLSR II (BD) and analyzed by FlowJo software (Tree Star).

Flowcytomix Assay.

The concentrations of chemokines in the supernatants from EBV-LCL culture were detected and analyzed with human chemokine assay kits (Bender MedSystems) as described before (Zheng et al., 2013b).

Statistical Analyses.

Data are expressed as means±SEM. The difference in cell death and viral copy for in vitro experiments, and intensity of florescence, tumor incidence, tumor size between PBS and treatment group were analyzed by impaired two-tailed Student's t test. The p value of difference for survival was determined by Kaplan-Meier log-rank test. p<0.05 was considered to be significant.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Epstein-Barr virus-induced lymphoproliferative disease (EBV-LPD) after transplantation remains a serious and life-threatening complication. In the examples provided, it is shown that aminobisphosphonate pamidronate (PAM)-expanded human Vγ9Vδ2-T cells efficiently killed EBV-transformed autologous lymphoblastoid B cell lines (EBV-LCL) through γ/δ-TCR and NKG2D receptor triggering, and Fas and TRAIL engagement. By inoculation of EBV-LCL in Rag2$^{-/-}$γc$^{-/-}$ mice and humanized mice, lethal EBV-LPD with characteristics close to the human disease were established. Adoptive transfer of PAM-expanded Vγ9Vδ2-T cells alone effectively prevented EBV-LPD in Rag2$^{-/-}$γc$^{-/-}$ mice and induced EBV-LPD regression in EBV$^+$ tumor-bearing Rag2$^{-/-}$γc$^{-/-}$ mice. PAM treatment inhibited EBV-LPD development in humanized mice through selective activation and expansion of Vγ9Vδ2-T cells. This study provides proof-of-principle for a therapeutic approach using PAM to control EBV-LPD through Vγ9Vδ2-T-cell targeting.

Example 1

Vγ9Vδ2-T Cells Kill EBV-LCL In Vitro

Figure 2B:
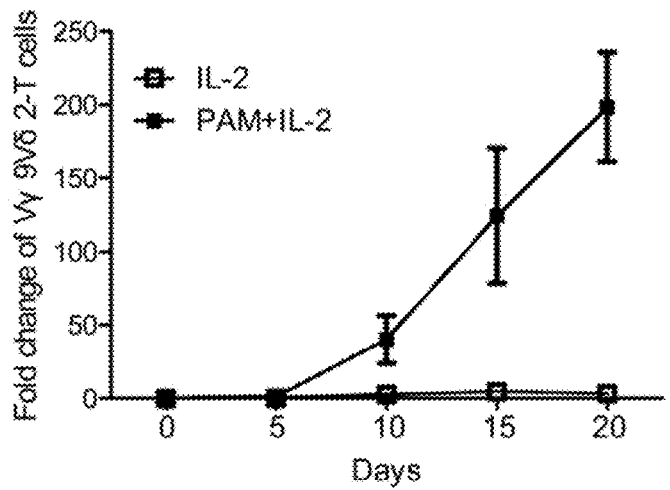
Figure 2C:
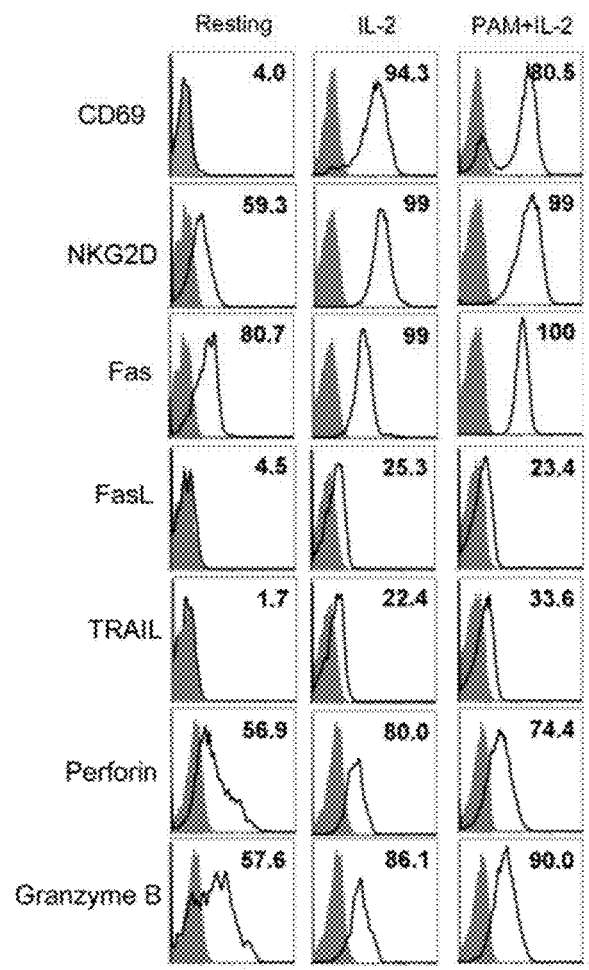
Figure 2D:
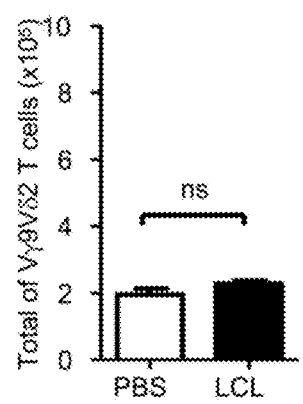

EBV-LCL showed enhanced expression of stress-inducible major histocompatibility complex class I-related proteins A and B (MICA/B), Fas and TNF-related apoptosis-inducing ligand (TRAIL) receptor 2 (DR5) expression, when compared to their normal autologous B cells (FIG. 1A). In contrast, both normal B cells and EBV-LCL had little or no FasL and TRAIL receptor 1 (DR4) expression on cell surface (FIG. 1A). Consistent with our previous reports (Li et al., 2013; Tu et al., 2011), pamidronate induced selective activation and expansion of Vγ9Vδ2-T cells, and up-regulation of the surface expressions of CD69, NKG2D, Fas ligand (FasL), TRAIL, and intracellular cytolytic granules, perforin and granzyme B, in Vγ9Vδ2-T cells (FIG. 2A-2C). In contrast, EBV-LCL alone could not efficiently expand Vγ9Vδ2-T cells from EBV-seropositive donors (FIG. 2D).

Figure 2E:
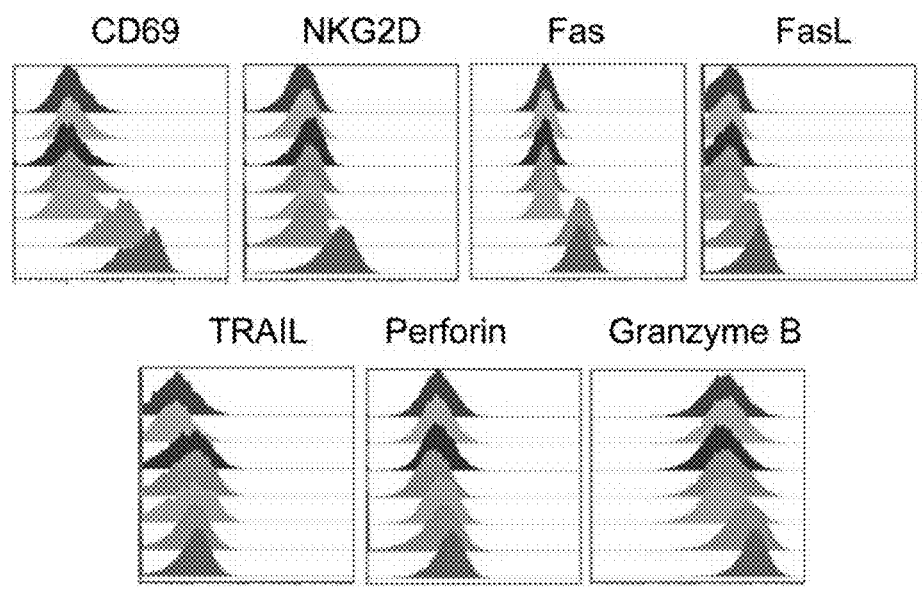

Pamidronate-expanded Vγ9Vδ2-T cells were purified by positive or negative selection with anti-TCRγ/δ MicroBead or TCRγ/δ$^+$ T cell isolation kit, and then co-cultured with autologous EBV-LCL. As shown in FIG. 1B, pamidronate-expanded Vγ9Vδ2-T cells sorted through negative selection only had minor cytotoxic activity against EBV-LCL, whereas pamidronate-expanded Vγ9Vδ2-T cells sorted through positive selection had significant higher cytotoxic activity against EBV-LCL. In addition, Vγ9Vδ2-T cells sorted through positive selection had higher CD69, Fas, FasL, TRAIL, granzyme B expressions than those sorted through negative selection (FIG. 2E). These results indicated that recent γ/δ-T cell receptor (TCR) engagement enhanced their activation and cytotoxicity against EBV-LCL.

Pamidronate-expanded Vγ9Vδ2-T cells sorted through positive selection displayed potent cytotoxicity against EBV-LCL in a dose-dependent manner, but showed limited if any killing activity against normal B cells (FIG. 1C). This cytotoxicity required cell-cell direct contact, as indicated by Transwell experiments (FIG. 1D). The immobilized recombinant MICA/B enhanced Vγ9Vδ2-T cell activation, especially for the cells sorted through positive selection, in terms of the expressions of CD69, NKG2D, Fas, FasL, TRAIL, perforin or granzyme B (FIG. 2E). The significant granule exocytosis, as evidenced by the increase of surface expression of CD107a, was also detected in Vγ9Vδ2-T cells upon the immobilized MICA/B stimulation (FIG. 1E). In parallel with granule exocytosis, the immobilized MICA/B significantly enhanced the cytotoxic activity of Vγ9Vδ2-T cells against EBV-LCL (FIG. 1F). Indeed, the levels of the granule exocytosis and cytotoxicity of Vγ9Vδ2-T cells sorted through positive selection were much higher than that in cells sorted through negative selection upon the immobilized MICA/B stimulation (FIGS. 1E and 1F). These data suggest MICA/B expressed EBV-LCL can enhance the activation and cytotoxic activity of Vγ9Vδ2-T cells especially those sorted through positive selection. Therefore, pamidronate-expanded Vγ9Vδ2-T cells purified with γ/δ-TCR positive selection were used for subsequent experiments.

Figure 2F:
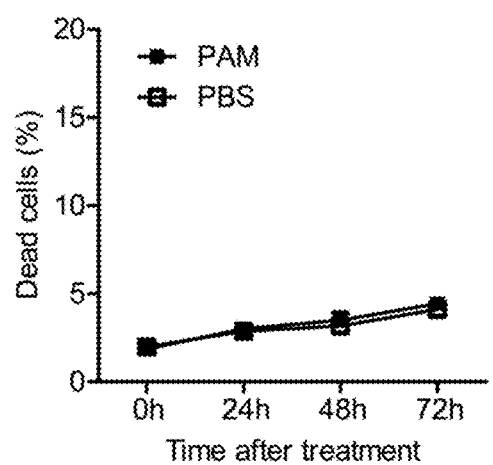
Figure 2G:
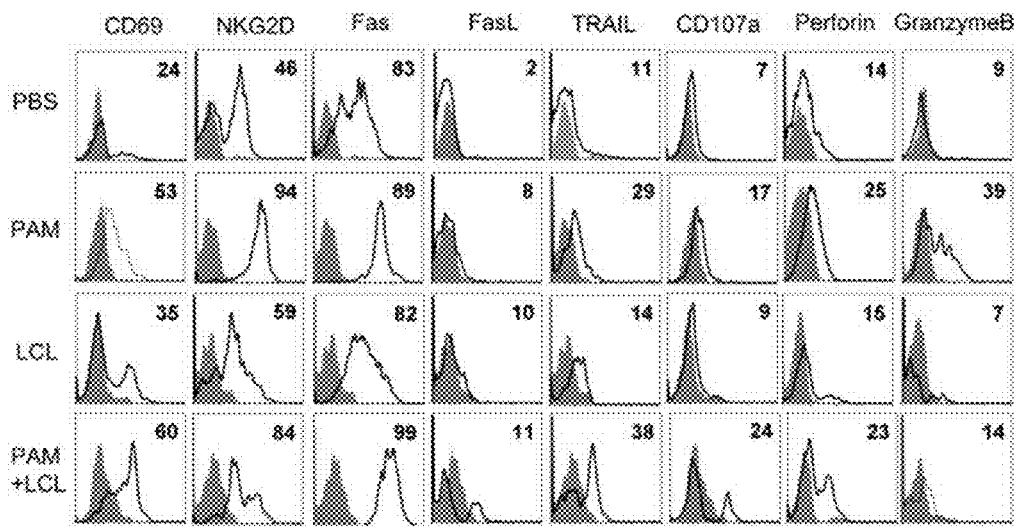

Blockade of NKG2D, FasL and TRAIL using appropriate neutralizing antibodies significantly inhibited the cytolytic activities of Vγ9Vδ2-T cells against EBV-LCL (FIG. 1G). To confirm the involvement of cytolytic granule release in the killing of EBV-LCL by Vγ9Vδ2-T cells, the perforin-specific inhibitor concanamycin A (CMA) and granzyme B inactivator Bcl-2 were used. As shown in FIG. 1G, cytolytic activity of Vγ9Vδ2-T cells against EBV-LCL was strongly inhibited after CMA or Bcl-2 treatment. These results indicate that the cytotoxicity of Vγ9Vδ2-T cells against EBV-LCL is dependent on NKG2D activation, and mediated by Fas-FasL, TRAIL-DR5 and perforin-granzyme B pathways. In addition, pamidronate alone did not show any cytotoxic activities against EBV-LCL (FIG. 2F), but it could enhance the expression of EBV-LCL recognition receptors and cytotoxic molecules in Vγ9Vδ2-T cells (FIG. 2G). Taken together, our results indicated that pamidronate-expanded Vγ9Vδ2-T cells can efficiently kill EBV-LCL.

Example 2

Vγ9V82 T Cells Prevent EBV-LPD in Rag2$^{-/-}$γc$^{-/-}$ Mice

Figure 3A:
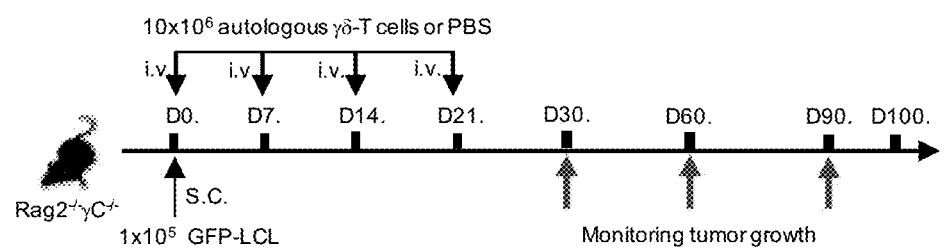
FIGS. 3A-3D show that Vγ9Vδ2-T cells prevent EBV-LPD in Rag2⁻/⁻γc⁻/⁻ mice.

Human B cells infected with the EGFP-tagged EBV were used to establish EGFP$^+$ EBV-LCL in order to monitor the growth of EBV-LCLs in vivo. The EBV-LPD model was further established in the Rag2$^{-/-}$γc$^{-/-}$ immunodeficient mice after subcutaneous (s.c.) inoculation of EGFP-expressing EBV-LCL (0.1×10$^6$/mouse) (FIG. 3A) (Lacerda et al., 1996). To determine whether human Vγ9Vδ2-T cells could prevent EBV-LPD in vivo, highly purified (>97%) pamidronate-expanded autologous Vγ9Vδ2-T cells (10×10$^6$ cells/mouse) were adoptively transferred intravenously (i.v.) into Rag2$^{-/-}$γc$^{-/-}$ mice at day 0, 7, 14 and 21 post EGFP-expressing EBV-LCL inoculation (FIG. 3A). PBS-treated mice were used as controls.

After inoculation with EBV-LCL, all control mice developed EBV-LPD. The rapid growth of EBV-LCL was detected subcutaneously in PBS-treated mice by in vivo imaging after inoculation with EBV-LCL, and all control mice developed subcutaneous solid tumors. Histologically, these tumors were immunoblastic lymphomas and derived from human B cells as evidenced by positive staining for human CD20. The tumor cells had high expression levels of EBV latent membrane protein 1 (LMP1) and small EBV-encoded RNAs type 1/2 (EBER-1/2) expressions. Furthermore, tumor metastases in liver, kidney and lung were evidenced by histological and immunophenotypic analysis for CD20, LPM1 and EBER-1/2 expression. As a result, 9 of 11 (82%) PBS-treated mice died within 60 days post EBV-LCL inoculation (FIG. 3B).

Figure 3B:
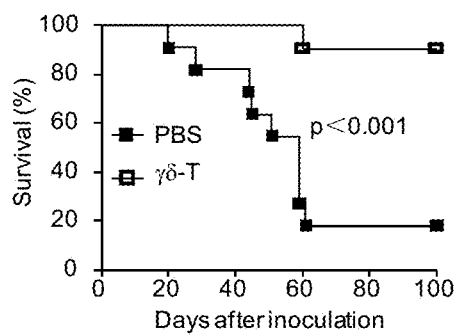
Figure 3C:
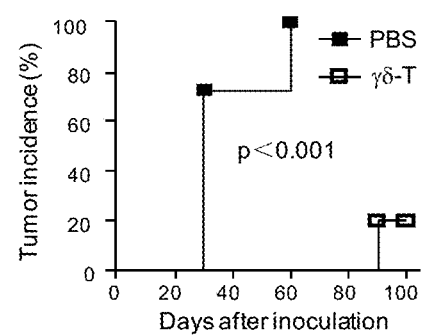
Figure 3D:
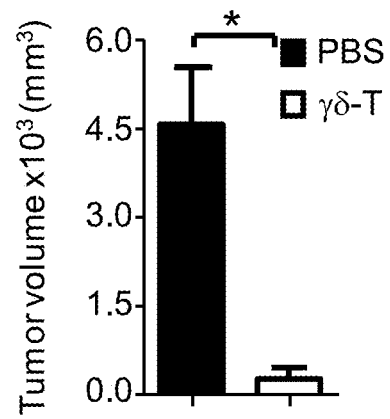
Figure 4:
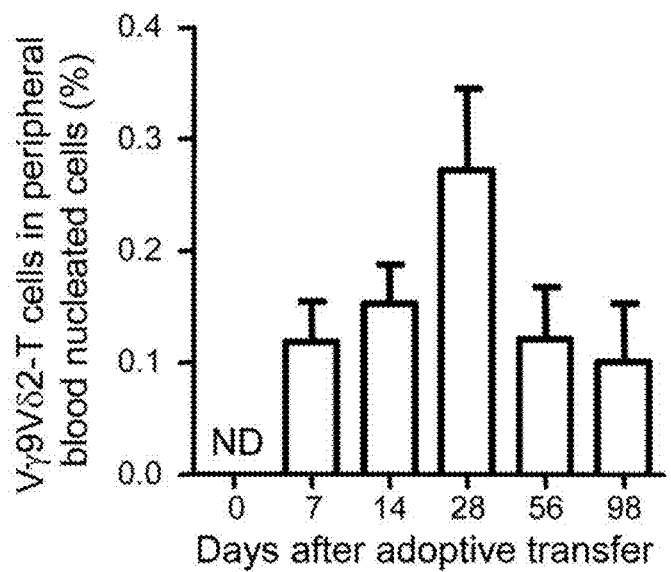
FIG. 4 shows the frequency of Vγ9Vδ2-T cells in peripheral blood of EBV-LCL-grafted Rag2⁻/⁻γc⁻/⁻ mice. After adoptive transfer of Vγ9Vδ2-T cells in EBV-LCL-grafted Rag2⁻/⁻γc⁻/⁻ mice (n=5), the frequencies (mean±SEM) of Vγ9Vδ2-T cells in the peripheral blood nucleated cells were monitored and shown. ND, not detectable.

Adoptive transfer of Vγ9Vδ2-T cells significantly enhanced survival of EBV-LCL-grafted immunodeficient mice (FIG. 3B). Indeed only 1 out of 10 mice with adoptively transferred Vγ9Vδ2-T cells died during the 100 day-observation period (FIG. 3B), and only 2 out of 10 mice developed subcutaneous solid tumors after 90 days of EBV-LCL inoculation (FIG. 3C). After adoptive transfer of Vγ9Vδ2-T cells, these cells could persist for up to 98 days in the peripheral blood in the EBV-LCL-grafted mice (FIG. 4). Histological and immunophenotypic analysis of CD20, LPM1 and EBER-1/2 expression showed no evidence of tumor metastases in liver, kidney and lung at autopsy in Vγ9Vδ2-T cells-treated mice after 100 days post EBV-LCL inoculation except in one mouse that died at day 60. Importantly, the volume of subcutaneous tumors in mice receiving Vγ9Vδ2-T cells was significantly reduced, when compared to PBS-treated mice (FIG. 3D). Histological and immunophenotypic analysis of the residual tumors further showed that the B-cell lymphomas had less Ki67-positive cells in mice receiving Vγ9Vδ2-T cells than that in PBS-treated mice, indicating the residual tumor cells in Vγ9Vδ2-T cell-treated mice had lower proliferative capacity than that in PBS-treated mice. These data demonstrated that pamidronate-expanded Vγ9Vδ2-T cells alone can effectively prevent EBV-LPD in $Rag2^{-/-}\gamma c^{-/-}$ mice.

Example 3

Figure 5A:
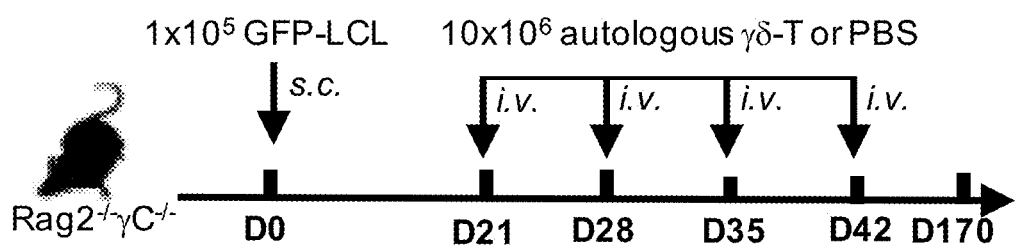
FIGS. 5A-5C show that Vγ9Vδ2-T cells induce the regression of EBV-LPD in tumor-bearing Rag2$^{-/-}$γc$^{-/-}$ mice.
Figure 5B:
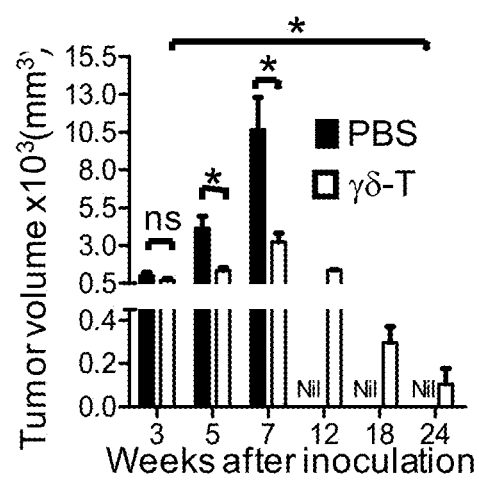
Figure 5C:
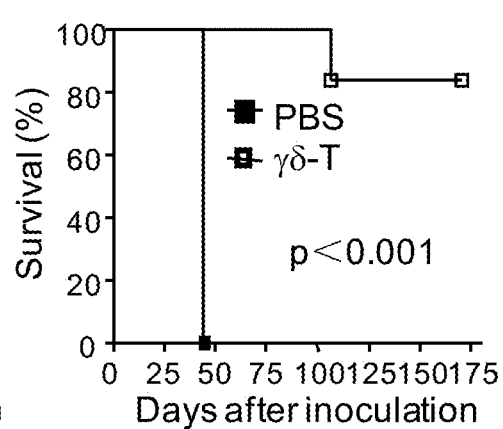

Vγ9Vδ2-T Cells Induce the Regression of EBV-LPD in Tumor-Bearing $Rag2^{-/-}\gamma c^{-/-}$ Mice To determine whether Vγ9Vδ2 T cells have therapeutic effect on EBV-LPD in mice, EGFP-expressing EBV-LCL ($0.1\times10^6$/mouse) were inoculated into $Rag2^{-/-}\gamma c^{-/-}$ mice s.c. (FIG. 5A). Twenty one days later, all the mice had developed large subcutaneous tumors (medium surface area, 137 mm$^2$) as detected by in vivo imaging (FIG. 5B). Then half of these tumor-bearing mice were adoptively transferred with highly purified pamidronate-expanded autologous Vγ9Vδ2-T cells ($10\times10^6$ cells/mouse) i.v. at day 21, 28, 35 and 42, and another half of these tumor-bearing mice were treated with PBS as the control (FIG. 5A). PBS-treated mice had subcutaneous tumor with progressive growth and extension to the abdominal cavity, liver and kidney (data not shown), ultimately causing death within 43 days after EBV-LCL inoculation (FIG. 5B-5C). In contrast, Vγ9Vδ2-T-cell treatment constrained tumor growth, and only 1 of 6 mice died at day 107 post EBV-LCL inoculation (FIGS. 5B and 5C). The other 5 of 6 Vγ9Vδ2-T-cell-treated mice were still alive more than 170 days post EBV-LCL inoculation (FIG. 5C). In addition, Vγ9Vδ2-T cell treatment significantly reduced the volume of the subcutaneous tumors in these 5 mice (FIG. 5B). At day 170, the surviving 5 mice were killed and full necropsies performed, and no evidence of tumor metastasis in other organs was found in these surviving mice. In contrast to the intact B-cell lymphomas with numerous Ki67-positive cells in PBS-treated mice, histological and immunophenotypic analysis showed large areas of necrosis with calcification and interlaced fibrous tissue and scarce Ki67-positive cells in some residual tumors from Vγ9Vδ2-T cell-treated mice. These results indicated that pamidronate-expanded Vγ9Vδ2-T cells can induce the regression of EBV-LPD in $Rag2^{-/-}\gamma c^{-/-}$ mice.

Example 4

Vγ91762-T Cells Preferentially Home to Subcutaneous Tumor Sites

Figure 7A:
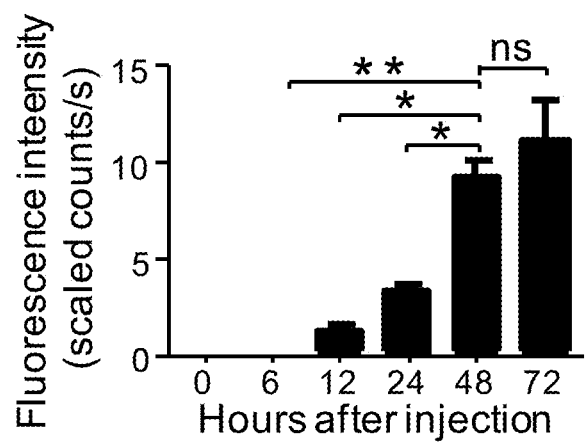
FIGS. 7A-7E show the homing program of Vγ9Vδ2-T cells in tumor-bearing Rag2$^{-/-}$γc$^{-/-}$ mice.

To evaluate the homing of Vγ9Vδ2-T cells to subcutaneous tumor site, highly purified pamidronate-expanded autologous Vγ9Vδ2-T cells were labeled with a lipophilic dye (DiR), and then injected i.v. into tumor-bearing mice established with EGFP-expressing EBV-LCL. In vivo imaging showed that DiR-labeled Vγ9Vδ2-T cells migrated to the tumor sites from 12 hr post injection and accumulated to peak level around the tumor sites at 72 hr post injection of Vγ9Vδ2-T cells (FIG. 7A). Confocal fluorescence microscope analysis in tumor sections revealed that Vγ9Vδ2-T cells infiltrated tumors 12 hr after injection. These data demonstrated that Vγ9Vδ2-T cells can preferentially migrate to subcutaneous tumor sites in mice.

Figure 7B:
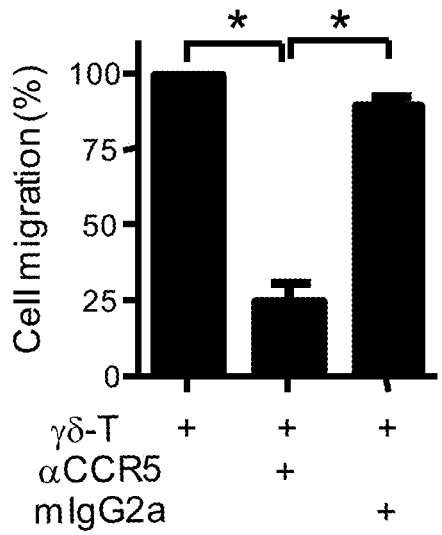
Figure 7C:
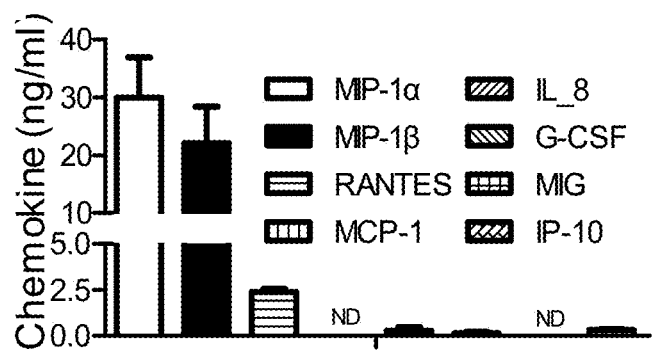
Figure 7D:
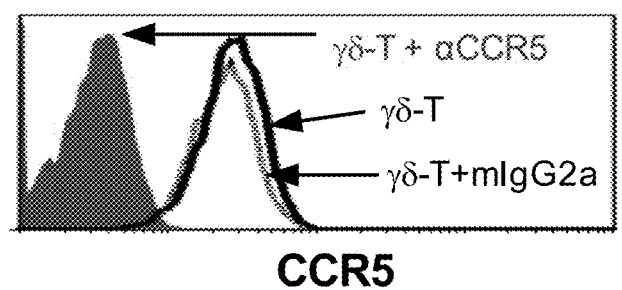
Figure 7E:
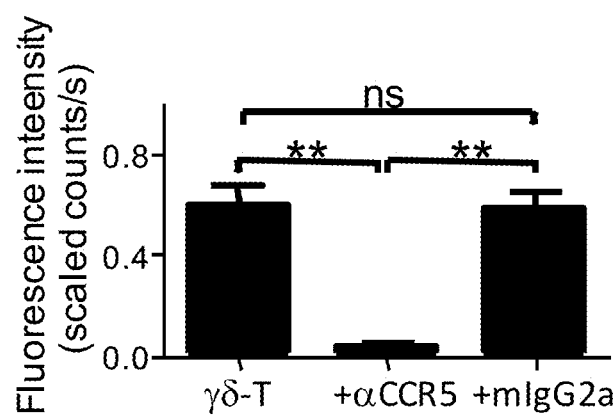

To determine the mechanisms related to the migration of Vγ9Vδ2-T cells, chemokine production in EBV-LCL and chemokine receptor expression in Vγ9Vδ2-T cells were examined. EBV-LCL secreted relatively high levels of CCR5 ligands, i.e. MIP-1α (CCL3), MIP-1β (CCL4) and RANTES (CCL5), but only little or no other chemokines (MCP-1, IL-8, G-CSF, MIG and IP-10) (FIG. 7C). Most Vγ9Vδ2-T cells expressed CCR5. The migration induced by supernatant from EBV-LCL was abrogated by CCR5 neutralizing antibody in a transwell chemotaxis assay (FIG. 7B). In vivo imaging further showed that the migration of Vγ9Vδ2-T cells to tumor sites was significantly prevented when the CCR5 was blocked by its neutralizing antibody (FIGS. 7D and 7E). These results demonstrated that the migration of Vγ9Vδ2-T cells to tumor sites was mainly mediated by CCR5 and its ligands.

Example 5

Pamidronate Controls the Development of EBV-LPD in Humanized Mice

Figure 8A:
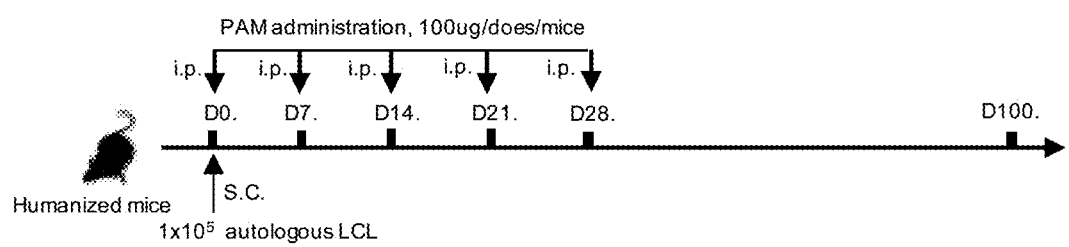
FIGS. 8A-8D show that pamidronate controls the development of EBV-LPD in humanized mice.

It was previously demonstrated that pamidronate could selectively expand human Vγ9Vδ2-T cells, but had no such effect on any other cell subset, such as CD4, CD8, B or NK cells in vitro and in humanized mice (Tu et al., 2011). We then investigated whether pamidronate could control EBV-LPD in humanized mice with stable reconstitution of huPBMC by expanding Vγ9Vδ2-T cells in vivo. After inoculation with EBV-LCL ($1\times10^5$/mouse) s.c., humanized mice were injected intraperitoneally (i.p.) with pamidronate (10 mg/kg body weight) at day 0, 7, 14, 21 and 28 post EBV-LCL inoculation (FIG. 8A). PBS-treated mice were used as controls. Similar to $Rag2^{-/-}\gamma c^{-/-}$ mice, all PBS-treated humanized mice developed EBV-LPD with subcutaneous tumors after EBV-LCL inoculation. These tumor cells were positive for human CD20, LMP1 and EBER-1/2. As in $Rag2^{-/-}\gamma c^{-/-}$ mice, tumor metastases were found in liver, kidney and lung in humanized mice. Due to EBV-LPD, all humanized mice died within 100 days of observation.

Figure 6:
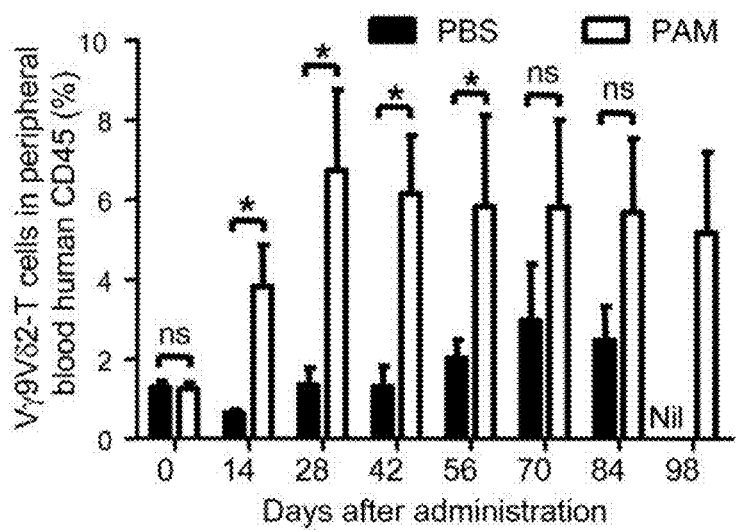
FIG. 6 shows the frequency of Vγ9Vδ2-T cells in the peripheral blood in EBV-LCL-grafted humanized mice. After treatment with pamidronate (PAM, n=8) or PBS (n=7) in EBV-LCL-grafted humanized mice, the frequencies (mean±SEM) of Vγ9Vδ2-T cells in the peripheral blood human CD45$^+$ cells were monitored and shown. ns, no significant; *p<0.05.
Figure 8B:
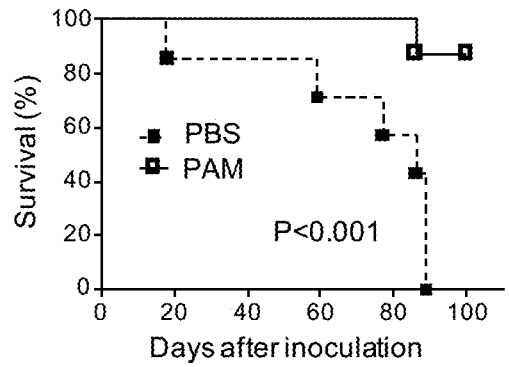
Figure 8C:
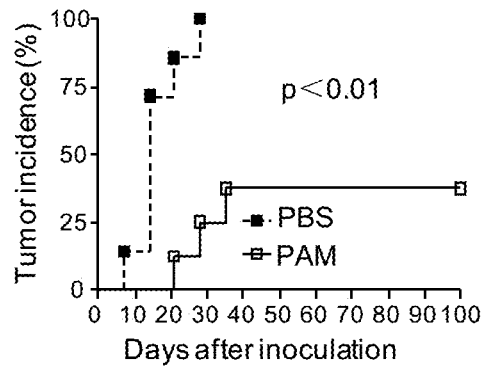
Figure 8D:
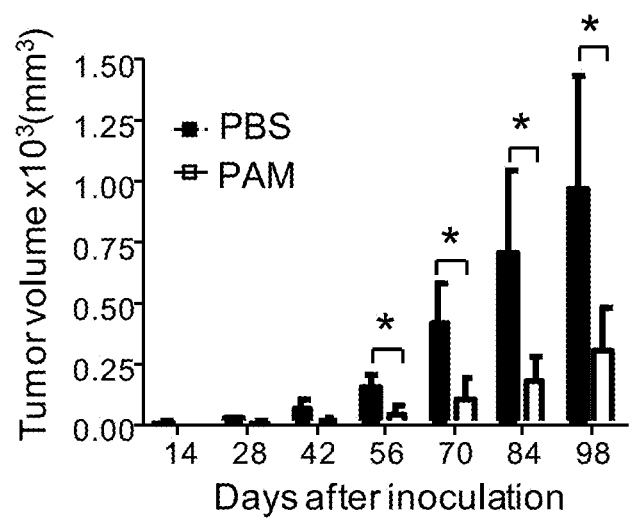

Treatment with pamidronate significantly increased the frequency of Vγ9Vδ2-T cells in the peripheral blood, and the cells could persist for up to 98 days in EBV-LCL-grafted humanized mice (FIG. 6). Pamidronate treatment also significantly prolonged the survival of humanized mice (FIG. 8B). In the pamidronate treatment group, only 1 out of 8 (12.5%) mice died and 3 out of 8 mice (37.5%) had subcutaneous tumor growth within 100 days. Importantly, humanized mice receiving pamidronate treatment had significantly lower tumor incidence and reduced tumor volume, compared with PBS-treated humanized mice (FIGS. 8C and 8D). At day 100, the surviving 7 mice were killed and full necropsies failed to show any evidence of tumor metastasis in other organs. Histological and immunophenotypic analysis of the residual tumors showed that the B-cell lymphomas had less Ki67-positive cells in mice receiving Vγ9Vδ2-T cells than that in PBS-treated mice, indicating the residual tumor cells in Vγ9Vδ2-T cell-treated mice had lower proliferative capacity than that in PBS-treated mice. These data demonstrated that pamidronate can effectively control the development of EBV-LPD in humanized mice.

Example 6

Pamidronate Cannot Control EBV-LPD in Humanized Mice without Vγ9Vδ2-T Cells

Figure 9C:
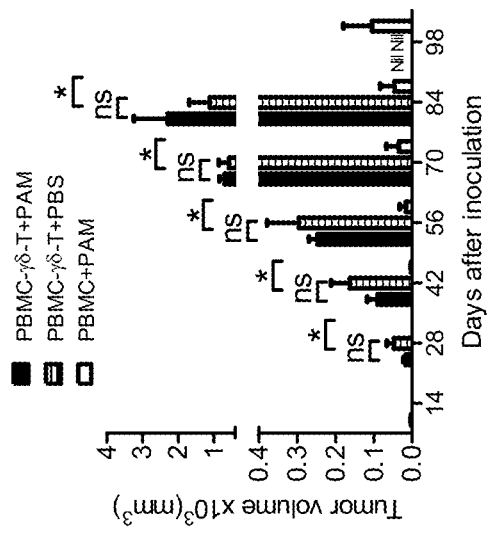
FIGS. 9A-9C show that pamidronate cannot control EBV-LPD in humanized mice without Vγ9Vδ2-T cells. Vγ9Vδ2-T-cell-depleted huPBMC were obtained after double depletions of Vδ2-T cells by positive selection with magnetic microbeads. Rag2$^{-/-}$γc$^{-/-}$ mice were transplanted with whole huPBMC or Vγ9Vδ2-T-cell-depleted huPBMC from the same healthy human donor. In contrast with the mice reconstituted with whole huPBMC, there was an absence of or scanty human Vγ9Vδ2-T cells in the mice reconstituted with Vγ9Vδ2-T-cell-depleted huPBMC. Humanized mice reconstituted with whole huPBMC (PBMC) or Vγ9Vδ2-T-cell-depleted huPBMC (PBMC-γδ-T) were inoculated with EBV-LCL and treated with pamidronate or PBS according to the protocol shown in FIG. 8A. The survival (FIG. 9A), tumor incidence (FIG. 9B) and tumor volume (FIG. 9C) in humanized mice (PBMC+PAM, n=12; PBMC-γδ-T+PAM, n=7; PBMC-γδ-T+PBS, n=6) are shown. Data are means±SEM; ns, not significant; *, p<0.05.
Figure 9B:
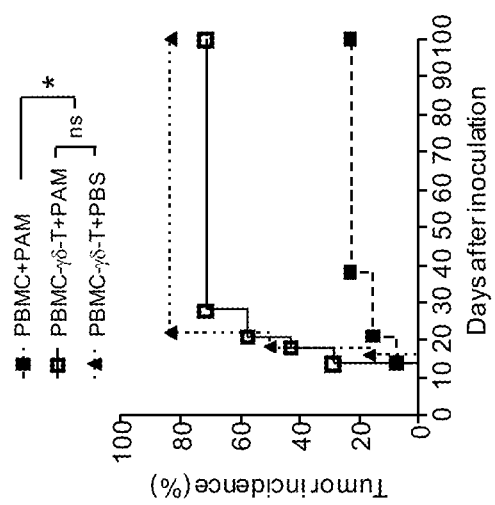
Figure 9A:
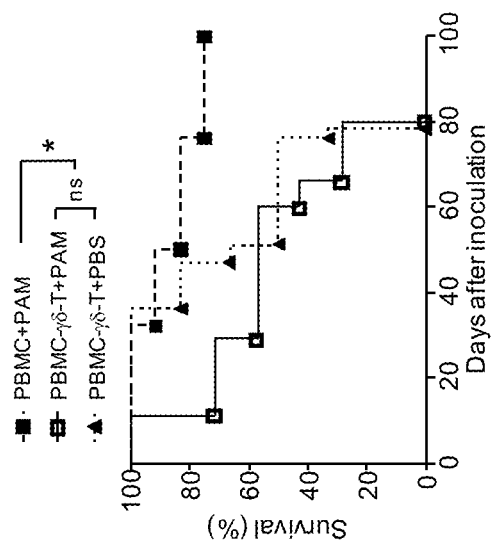

To further determine whether the control of EBV-LPD by pamidronate was mediated through Vγ9Vδ2-T cells in humanized mice, mice reconstituted Vγ9Vδ2-T-cell-depleted huPBMC were used (Tu et al., 2011). Mice reconstituted with whole huPBMC or Vγ9Vδ2-T-cell-depleted huPBMC were inoculated with EBV-LCLs s.c. and injected with pamidronate (10 mg/kg body weight) i.p. at day 0, 7, 14, 21 and 28 post EBV-LCL inoculation. Treatment with pamidronate significantly prolonged survival (FIG. 9A), reduced tumor occurrence (FIG. 9B) and decreased tumor volume (FIG. 9C) in humanized mice with whole huPBMC. In contrast, pamidronate had no such effects in humanized mice reconstituted with Vγ9Vδ2-T-cell-depleted huPBMC. These results demonstrated that the control of EBV-LPD in humanized mice by pamidronate is mainly mediated by a Vγ9Vδ2-T-cell dependent mechanism.

Example 7

Expansion of Vγ9Vδ2-T Cells

Figure 10A:
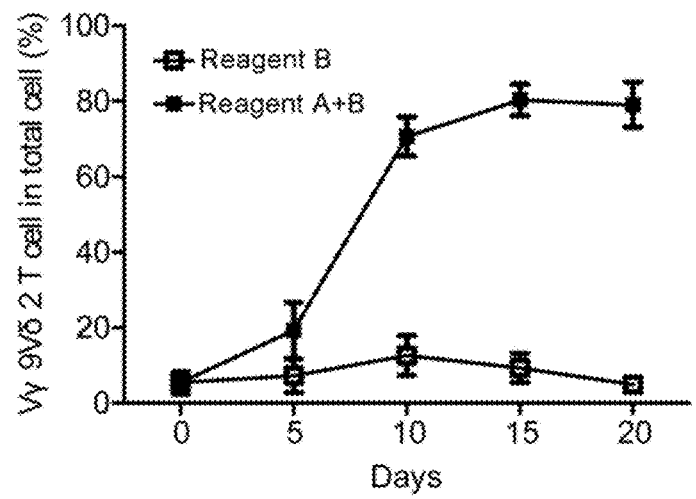
FIGS. 10A-10B. Vγ9Vδ2-T cells only accounted for 1-5% (mean, 3%) in the peripheral blood PBMC from randomly selected samples (FIG. 10A).
Figure 10B:
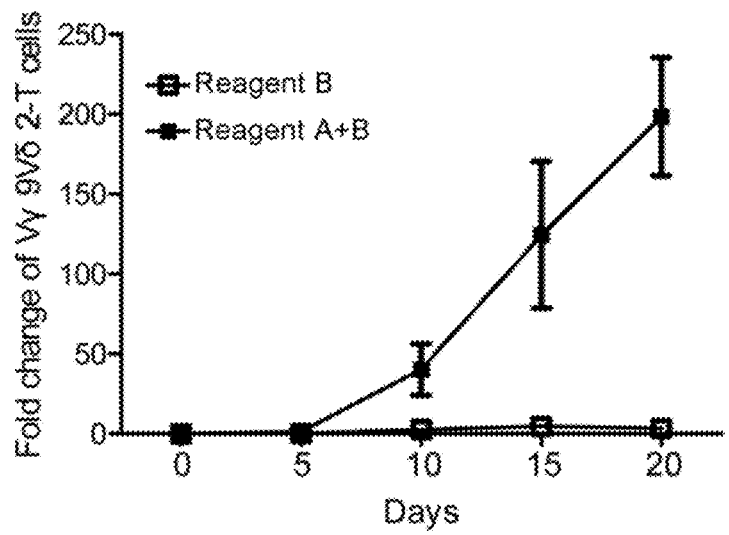

Human PBMCs were isolated from buffy coat preparation or anticoagulated peripheral blood by Ficoll-paque (GE Health life Science) gradient centrifugation. The PBMCs were cultured in 10% FBS-RPMI1640 supplemented with 15 ul of expansion reagent A; 25 ul of expansion reagent B was added from day 3 post culture. The percentages and fold changes of Vγ9Vδ2-T cells in whole culture cells were examined by flow cytometry using detection reagent A and C (FIGS. 10A-10B). Vγ9Vδ2-T cells only accounted for 1-5% (mean, 3%) in the peripheral blood PBMC from randomly selected samples (FIG. 10A). Post 20 days of in vitro culture in the presence of PAM and IL-2, the percentage of Vγ9Vδ2-T cells within the PBMCs increased to 67-95% (mean, 82%) and the Vγ9Vδ2-T cells were expanded by 156-309-fold (mean, 198-fold) (FIGS. 10A and 10B). Data are representative for 4 independent experiments. By contrast, the IL-2 could not induce the expansion of Vγ9Vδ2-T cells in the absence of PAM (FIGS. 10A and 10B).

Fresh PBMCs were cultured in the presence of expansion reagents for 20 days. Cells were further purified by selection reagent A and B. The purity of in-vitro expanded Vγ9Vδ2-T cells following selection kit was consistently over 97%.

Figure 11A:
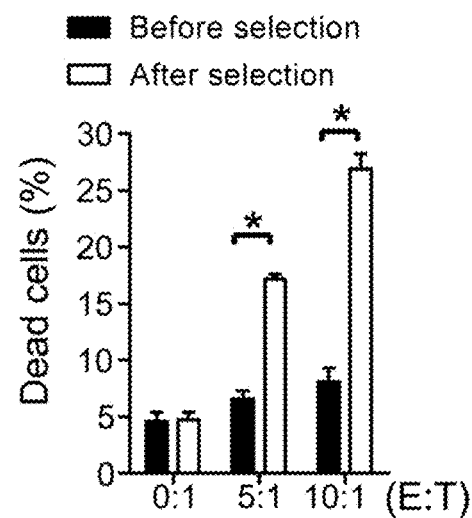
FIGS. 11A-11B.
Figure 11B:
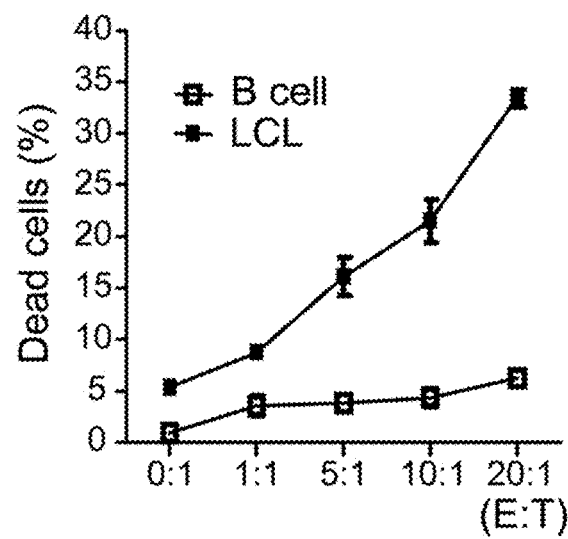

Before and after purification by selection reagent A and B, expansion kit-expanded Vγ9Vδ2-T cells were cultured with the autologous EBV-LCLs at different ratios for 4 hours (FIG. 11A). Expansion kit-expanded Vγ9Vδ2-T cells purified by selection reagents were cocultured with autologous EBV-LCL or normal B cells at different E:T ratios. The percentages of dead LCLs among the target cells (CD3$^-$ population) identified as CD3$^-$ and PI$^+$ for 4 independent experiments are shown in FIG. 11B. Hence, selected Vγ9Vδ2-T cells efficiently recognize and kill tumor cells (EBV-LCLs) in vitro. Vγ9Vδ2-T cells displayed potent killing capability against autologous EBV-LCLs. The cytotoxicity was in a dose-dependent manner as well (FIG. 11B). For EBV-transformed human B cells (target, T), Vγ9Vδ2-T cells (effector, E) killed up to 35% of EBV-LCLs at an E/T ratio of 20:1 even after 4 h of co-culture. However, the activated Vγ9Vδ2-T cells did not show significant cytotoxic activity when co-culture with normal human B cells.

Discussion

Immunodeficient mice are widely used as a pre-clinical model of EBV studies because these mice inoculated with human EBV-LCL can rapidly develop lethal human EBV-LPD with characteristics similar to those arising in immunocompromised patients (Funakoshi et al., Blood 83:2787-2794 (1994); Lacerda et al., 1996). By inoculation of human EBV-LCL in immunodeficient Rag2$^{-/-}$γc$^{-/-}$ mice, we established lethal EBV-LPD in these mice. Using this model, we demonstrated that adoptive transfer of pamidronate-expanded human Vγ9Vδ2-T cells alone not only effectively prevented EBV-LPD in Rag2$^{-/-}$γc$^{-/-}$ mice, but also induced the regression of EBV-LPD in EBV-induced tumor-bearing Rag2$^{-/-}$γc$^{-/-}$ mice. The lack of a human immune system in Rag2$^{-/-}$γc$^{-/-}$ mice hampers assessment of the pathogenesis, prevention and treatment of EBV-LPD, but this can be circumvented by reconstitution with huPBMC or CD34$^+$ stem cells (Lim et al., Blood 109:1043-1050 (2007); Ma et al., J. virology 85:165-177 (2011)). Recently we had established humanized mice with functional human immune system by reconstitution of huPBMC in Rag2$^{-/-}$γc$^{-/-}$ mice (Tu et al., 2011; Zheng et al., 2013b). These humanized mice contain functional human T and B cells, including a similar percentage of Vγ9Vδ2-T cells in peripheral blood as seen in humans (Tu et al., 2011; Zheng et al., 2013b). In this study, we further induced lethal EBV-LPD in these humanized mice by inoculation of human EBV-LCL and showed in this model that pamidronate treatment inhibited development of EBV-LPD through selective activation and expansion of Vγ9Vδ2-T cells in vivo.

Although it has been showed that human γδ-T cells have antiviral and antitumor activities (Bonneville et al., Nature reviews Immunology 10:467-478 (2010); Kabelitz et al., Cancer Res 67:5-8 (2007)), data supporting their reactivity towards EBV are still scarce (Kong et al., Blood 114:310-317 (2009); Kotsiopriftis et al., J. Virol. 79:7255-7261 (2005)). While one study have described in vitro recognition of EBV-LCL by Vδ1$^+$γδ-T cell clones (Orsini et al., Eur. J. Immunol. 24:3199-3204 (1994)), EBV-LCL are classically used as negative controls in in vitro cytotoxicity assays using Vγ9Vδ2-T cells. Accordingly, we confirmed lack of EBV-LCL killing by pamidronate expanded Vγ9Vδ2-T cells sorted by negative selection but unexpectedly unveiled significant cytotoxicity against EBV-LCL by the same cell subset after positive sorting using anti-TCR mAb. This suggests that recently activated Vγ9Vδ2-T cells can trigger the cytotoxic activity against EBV-LCL soon after TCR engagement. Our results further indicate that this process requires cell-cell contact and involves engagement of NKG2D on Vγ9Vδ2-T cells with MICA/B expressed on EBV-LCL. Indeed, we also found that the immobilized MICA/B enhanced Vγ9Vδ2-T cell activation, granule exocytosis and cytotoxic activity. Importantly, upon the immobilized MICA/B stimulation, the levels of the granule exocytosis and cytotoxicity of Vγ9Vδ2-T cells sorted by negative selection were much lower than that in the same cells after positive sorting using anti-TCR mAb. Therefore, both TCR-γ/δ and NKG2D are required for the recognition of Vγ9Vδ2-T cells and TCR-γ/δ engagement is essential for triggering their cytotoxic activity against EBV-LCL.

In line with our previous results using influenza virus-infected cells (Qin et al., 2009), we also found that the cytotoxic activity of Vγ9Vδ2-T cells against EBV-LCL involved engagement of the death-inducing Fas receptor, and release of cytotoxic effector molecules, such as perforin and granzyme. We further demonstrated that interaction of another death-inducing receptor DR5 expressed by EBV-LCL with TRAIL expressed on Vγ9Vδ2-T cells also enhanced Vγ9Vδ2-T cell-mediated EBV-LCL killing. Importantly, these pamidronate-expanded Vγ9Vδ2-T cells could migrate to tumor site and infiltrate into tumor tissues in vivo, and thus contributing to the control of EBV-LPD in mice. Consistent with our previous findings in chemotaxis assay using influenza virus-infected cells (Qin et al., 2011), using both transwell chemotaxis and in vivo imaging assays, here we further showed that the migration of Vγ9Vδ2-T cells to tumor sites was mainly mediated by CCR5 and its ligands. Taken together, our results indicate that pamidronate-expanded Vγ9Vδ2-T cells can control EBV-LPD by killing EBV-LCL.

Previous data showed that pamidronate-expanded Vγ9Vδ2-T cells can produce a large amount of IFN-γ (Qin et al., 2011). One study also demonstrated that IFN-γ secreted from NK cells can delay latent EBV antigen expression, and thus resulting in decreased the EBV-induced B cell proliferation (Strowig et al., PLoS Pathog 4:e27 (2008)). Indeed, here we also found the decreased proliferative capacity of tumor cells in Vγ9Vδ2-T-cell- and pamidronate-treated mice, comparing with that in control mice. Therefore, besides their direct killing, Vγ9Vδ2-T cells might also contribute the prevention of the metastases by inhibiting the proliferation of EBV-LCL through their secreted IFN-γ.

Pamidronate-induced expansion of Vγ9Vδ2-T cells, but not other T cell subsets, both in vitro and in humanized mice has been shown (Das et al., Blood 98:1616-1618 (2001); Kunzmann et al., N. Engl. J. Med. 340:737-738 (1999); Sicard et al., J. immunology 175:5471-5480 (2005); Tu et al., 2011). Although non-Vγ9Vδ2 γδ T cells could be also activated by pamidronate, the frequencies of CD69 ', perforin', and granzyme B$^+$ cells in non-Vγ9Vδ2 γδ T cells were significantly lower than that in Vγ9Vδ2-T cells (Tu et al., 2011). Indeed, the adoptive transfer experiments in Rag2$^{-/-}$γc$^{-/-}$ ice further showed that pamidronate-expanded Vγ9Vδ2-T cells readily controlled EBV-LPD in vivo without the help from other human and murine T, B, and NK cells, which are absent in Rag2$^{-/-}$γc$^{-/-}$ mice. Importantly, pamidronate effectively controlled the development of EBV-LPD in humanized mice reconstituted with whole huPBMC, but had no such beneficial effects in mice reconstituted with Vγ9Vδ2-T-cell-depleted huPBMC. In addition, pamidronate did not show any cytotoxic activity against EBV-LCL. Therefore, this indicates that control of EBV-LPD by pamidronate in humanized mice is mainly mediated by Vγ9Vδ2-T cells.

As in humans, Vγ9Vδ2-T cells make up a small percentage of lymphocytes in humanized mice (Tu et al., 2011). The antitumor activity of Vγ9Vδ2-T cells are dependent on both Vγ9Vδ2-T cell frequency and degree of activation (Bonneville and Scotet, 2006). Therefore, we could not observe the difference of disease severity between mice reconstituted with whole huPBMC and Vγ9Vδ2-T-cell-depleted huPBMC. Indeed, the in vitro results also showed that EBV-LCL alone could not efficiently expand Vγ9Vδ2-T cells in EBV-seropositive donors. It was only in the presence of pamidronate that Vγ9Vδ2-T cells could be expanded and also induced to express sufficient levels of EBV-LCL recognition receptors as well as cytotoxic molecules to control the growth of EBV-LCL.

By contrast with results of adoptive transfer of EBV-specific CTL which lead to durable eradications of the tumors (Kanakry and Ambinder, 2013; Khanna et al., 1999; Leen et al., 2007; Rooney et al., 1995), here we showed in some mice that Vγ9Vδ2-T-cell-based therapy could not completely eradicate the primary tumors. The variations in frequency and activation of Vγ9Vδ2-T cells in different mice might account for this. Thus, it is important to adjust the dose of pamidronate in real-time according to results by monitoring the therapeutic effects and frequency of Vγ9Vδ2-T cells. Nevertheless, the strategy proposed in current study by using pamidronate to control EBV-LPD through boosting Vγ9Vδ2-T-cell immunity in vivo has obvious advantage because it may avoid the complicated procedures for generation of EBV-specific CTL in vitro.

In summary, the study demonstrated that pamidronate-expanded Vγ9Vδ2-T cells can directly kill the EBV-LCL in vitro and in vivo, and pamidronate can control EBV-LPD in humanized mice through a Vγ9Vδ2-T-cell dependent mechanism. The study provides a strong preclinical proof of principle for a novel therapeutic approach using pamidronate to boost human Vγ9Vδ2-T-cell immunity against EBV-LPD. Pamidronate is commonly used clinically for the treatment of osteoporosis and Paget's disease, and the use of a human equivalent dose of pamidronate can effectively control EBV-LPD in humanized mice, suggesting rapid translation to human clinical trials. This 'new application of an old drug' potentially offers a safe and readily available option for the treatment of EBV-LPD.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of treating a subject having an Epstein-Barr virus (EBV)-associated disorder, comprising administering to the subject an effective amount of aminobisphosphonate pamidronate (PAM) in an amount effective to increase the number of Vγ9Vδ2-T cells in the subject; wherein the EBV-associated disorder is caused by EBV; wherein the effective amount is at least about 10 mg/kg of body weight of the subject.

2. The method of claim 1, wherein the EBV-associated disorder is selected from lymphoproliferative disease (LPD), posttransplant lymphoproliferative disorder (PLPD), Hodgkin's disease, Burkitt's lymphoma, and nasopharyngeal carcinoma (NPC).

3. The method of claim 1, wherein the subject is a human.

4. The method of claim 1, wherein PAM is administered with a pharmaceutically acceptable carrier.

5. A method of treating a subject having an Epstein-Barr virus (EBV)-associated disorder, comprising administering to the subject an effective amount of Vγ9Vδ2-T cells that were first expanded with aminobisphosphonate pamidronate (PAM) and then purified by positive selection; wherein the EBV-associated disorder is caused by EBV; and
wherein the PAM-expanded Vγ9Vδ2-T cells purified by positive selection have increased cytotoxicity against infected cells when compared to cytotoxicity of PAM-expanded Vγ9Vδ2-T cells purified by negative selection.

6. The method of claim 5, wherein the subject is a human.

7. The method of claim 5, wherein the PAM-expanded and purified Vγ9Vδ2-T cells are administered with a pharmaceutically acceptable carrier.

8. The method of claim 1, wherein the effective amount is administered more than once, more than twice, more than three times, or more than four times to the subject.

9. The method of claim 1, wherein the EBV-associated disorder is lymphoproliferative disease (LPD).

10. The method of claim 5, wherein the PAM-expanded and purified Vγ9Vδ2-T cells are activated Vγ9Vδ2-T cells.

11. The method of claim 10, wherein the activated Vγ9Vδ2-T cells are activated by T-cell receptor (TCR) engagement.

12. The method of claim 5, wherein the PAM-expanded and purified Vγ9Vδ2-T cells are administered more than once, more than twice, more than three times, or more than four times to the subject.

13. The method of claim 5, wherein the EBV-associated disorder is a disorder selected from the group consisting of lymphoproliferative disease (LPD), posttransplant lymphoproliferative disorder (PLPD), Hodgkin's disease, Burkitt's lymphoma, and nasopharyngeal carcinoma (NPC).

14. The method of claim 5, wherein the EBV-associated disorder is lymphoproliferative disease (LPD).

15. The method of claim 5, wherein the PAM-expanded and purified Vγ9Vδ2-T cells are activated Vγ9Vδ2-T cells, wherein the EBV-associated disorder is lymphoproliferative disease (LPD).

16. The method of claim 15, wherein the activated Vγ9Vδ2-T cells are activated by T-cell receptor (TCR) engagement.

17. A method of treating a subject having an Epstein-Barr virus (EBV)-associated disorder, comprising administering to the subject an effective amount of Vγ9Vδ2-T cells that were first expanded with aminobisphosphonate pamidronate (PAM) and then purified by positive selection;
wherein the EBV-associated disorder is caused by EBV;
wherein the PAM-expanded Vγ9Vδ2-T cells purified by positive selection have increased cytotoxicity against infected cells when compared to cytotoxicity of PAM-expanded Vγ9Vδ2-T cells purified by negative selection, and
wherein the increased cytotoxicity is at effector cell (E) to target cell (T) ratio of 5:1, 10:1, or 20:1.

18. The method of claim 17, wherein the infected cells are EBV-infected cells.

19. The method of claim 18, wherein the EBV-infected cells are EBV-infected B cells.

20. The method of claim 17, wherein the PAM-expanded Vγ9Vδ2-T cells purified by positive selection are not cytotoxic against uninfected cells.

21. The method of claim 1, wherein the increase in the number of Vγ9Vδ2-T cells in the subject produces an increase to therapeutically effective frequency of the Vγ9Vδ2-T cells in the subject.

\* \* \* \* \*